(12) United States Patent
Mizuguchi et al.

(10) Patent No.: US 11,969,023 B2
(45) Date of Patent: *Apr. 30, 2024

(54) CONTROL DEVICE FOR AEROSOL INHALATION DEVICE AND AEROSOL INHALATION DEVICE

(71) Applicant: JAPAN TOBACCO INC., Tokyo (JP)

(72) Inventors: Kazuma Mizuguchi, Tokyo (JP); Takeshi Akao, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 184 days.

This patent is subject to a terminal disclaimer.

(21) Appl. No.: 17/570,402

(22) Filed: Jan. 7, 2022

(65) Prior Publication Data

US 2022/0125121 A1 Apr. 28, 2022

Related U.S. Application Data

(63) Continuation of application No. 16/885,337, filed on May 28, 2020, now Pat. No. 11,490,661.

(30) Foreign Application Priority Data

May 31, 2019 (JP) ................................ 2019-102263

(51) Int. Cl.
*A24F 40/50* (2020.01)
*A61M 15/06* (2006.01)
*H02M 3/158* (2006.01)

(52) U.S. Cl.
CPC ............. *A24F 40/50* (2020.01); *H02M 3/158* (2013.01); *A61M 15/06* (2013.01)

(58) Field of Classification Search
None
See application file for complete search history.

(56) References Cited

U.S. PATENT DOCUMENTS 3,831,003 A 8/1974 Foerster
5,734,914 A 3/1998 Nakamura et al.
(Continued)

FOREIGN PATENT DOCUMENTS

CN 207251178 U 4/2018
CN 108430244 A 8/2018
(Continued)

OTHER PUBLICATIONS

U.S. Office Action dated Jul. 18, 2023 in U.S. Appl. No. 16/885,343, 34 pages.
(Continued)

*Primary Examiner* — Phu H Nguyen
(74) *Attorney, Agent, or Firm* — XSENSUS LLP

(57) ABSTRACT

Control device for aerosol inhalation device, includes operational amplifier including output terminal configured to generate voltage according to voltage applied to load configured to heat aerosol source and having correlation between temperature and electrical resistance value, control unit including input terminal and configured to perform processing based on voltage applied to the input terminal, and voltage dividing circuit configured to electrically connect the output terminal of the operational amplifier and the input terminal of the control unit. Power supply voltage of the operational amplifier is higher than power supply voltage of the control unit, and equals voltage applied to aerosol generation circuit including the load, and one of inverting input terminal and noninverting input terminal of the operational amplifier is electrically connected to the aerosol generation circuit.

14 Claims, 13 Drawing Sheets

(56) References Cited

U.S. PATENT DOCUMENTS

Figure 1A:
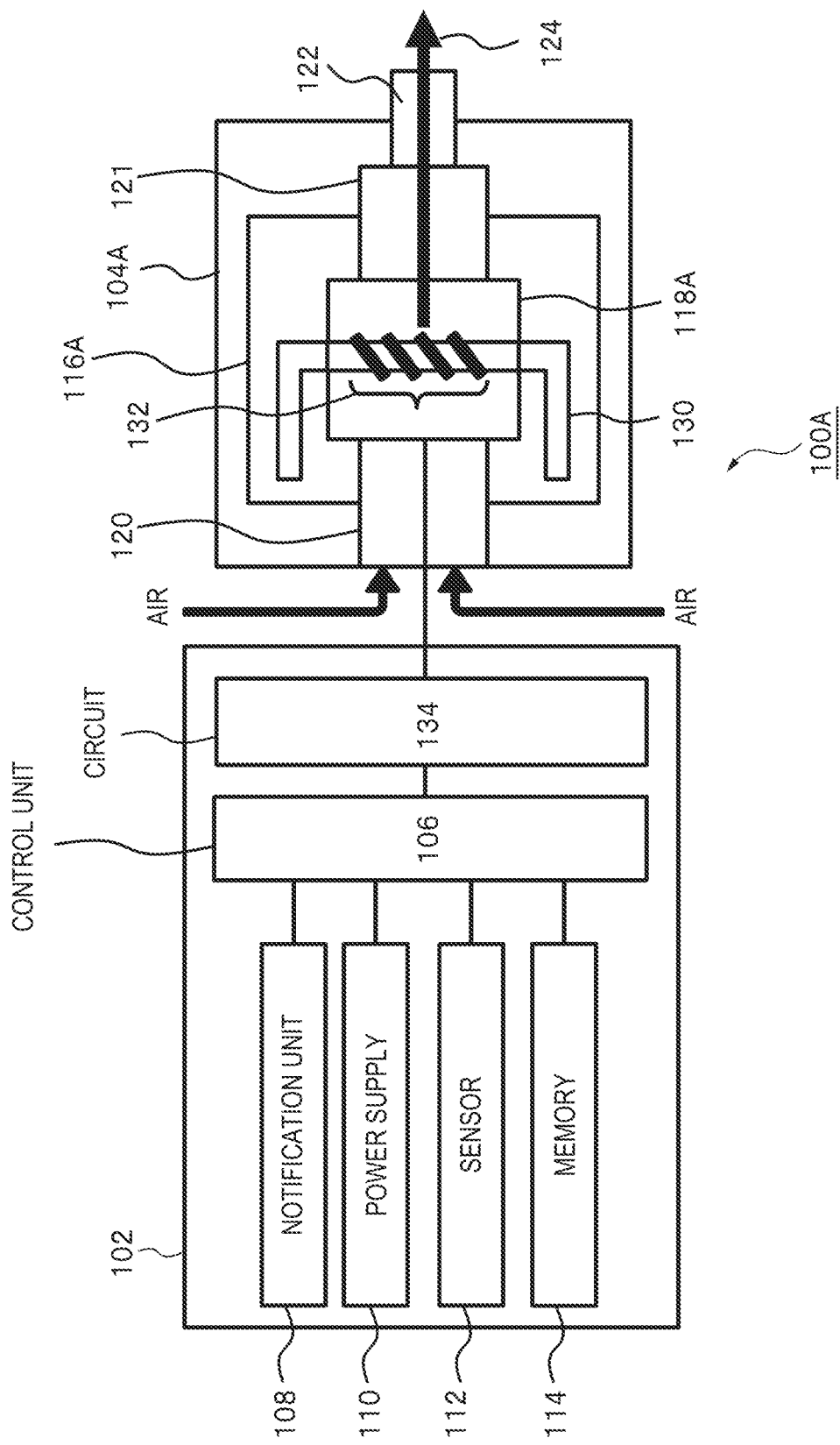

| | | |
|---|---|---|
| 10,932,495 B2 | 3/2021 | Reevell |
| 2004/0056210 A1 | 3/2004 | Scherer |
| 2015/0359263 A1 | 12/2015 | Bellinger |
| 2016/0174611 A1 | 6/2016 | Monsees et al. |
| 2016/0316822 A1 | 11/2016 | Liu |
| 2016/0374397 A1 | 12/2016 | Jordan et al. |
| 2017/0245553 A1 | 8/2017 | Reevell |
| 2017/0360097 A1 | 12/2017 | Xiang |
| 2018/0000160 A1 | 1/2018 | Taschner et al. |
| 2018/0027878 A1 | 2/2018 | Dendy et al. |
| 2018/0070641 A1 | 3/2018 | Batista et al. |
| 2019/0320717 A1 | 10/2019 | Tabasso et al. |
| 2020/0237005 A1 | 7/2020 | Lim et al. |
| 2020/0367570 A1 | 11/2020 | Batista et al. |
| 2021/0401061 A1 | 12/2021 | Davis et al. |

FOREIGN PATENT DOCUMENTS

| | | |
|---|---|---|
| CN | 208354611 U | 1/2019 |
| CN | 109730360 A | 5/2019 |
| JP | 60-047966 A | 3/1985 |
| JP | 03-030734 U | 3/1991 |
| JP | 08-241240 A | 9/1996 |
| JP | 11-227439 A | 8/1999 |
| JP | 2006-184241 A | 7/2006 |
| JP | 2009-159121 A | 7/2009 |
| JP | 2011-257928 A | 12/2011 |
| JP | 2014-501105 A | 1/2014 |
| JP | 2017-501805 A | 1/2017 |
| JP | 2017-503520 A | 2/2017 |
| JP | 2018-526983 A | 9/2018 |
| WO | 2012/085203 A1 | 6/2012 |
| WO | 2012/085207 A1 | 6/2012 |
| WO | 2015/045534 A1 | 4/2015 |
| WO | 2015/100361 A1 | 7/2015 |
| WO | 2017/015042 A1 | 1/2017 |
| WO | 2017/144191 A1 | 8/2017 |
| WO | 2017/144374 A1 | 8/2017 |
| WO | 2018/001746 A1 | 1/2018 |
| WO | 2019/082262 A1 | 5/2019 |
| WO | 2019/082264 A1 | 5/2019 |

OTHER PUBLICATIONS

U.S. Office Action dated May 13, 2022 in related U.S. Appl. No. 16/885,343, 37 pages.

Notification of Reasons for Refusal received for Japanese Patent Application No. 2019-102263, dated Sep. 6, 2019, 8 pages including English Translation.

Decision to Grant a Patent received for Japanese Patent Application No. 2019-102263, dated Jan. 29, 2020, 5 pages including English Translation.

Notification of Reasons for Refusal received for Japanese Patent Application No. 2019-102238, dated Aug. 14, 2019, 6 pages including English Translation.

Decision to Grant a Patent received for Japanese Patent Application No. 2019-102238, dated Oct. 7, 2019, 5 pages including English Translation.

Notification of Reasons for Refusal received for Japanese Patent Application No. 2019-102382, dated Jul. 16, 2019, 6 pages including English Translation.

Decision to Grant a Patent received for Japanese Patent Application No. 2019-102382, dated Nov. 7, 2019, 5 pages including English Translation.

Extended European search report dated Oct. 14, 2020, in corresponding European patent Application No. 20176500.5, 11 pages.

Extended European Search Report dated Oct. 22, 2020 in European Patent Application No. 20176507.0, 9 pages.

Extended European search report dated Oct. 28, 2020, in corresponding European patent Application No. 20176508.8, 11 pages.

Office Action dated Nov. 18, 2020, in corresponding U.S. Appl. No. 16/885,343, 14 pages.

Chinese Office Action dated Apr. 28, 2021, concerning Chinese Patent Application No. 202010459771.2.

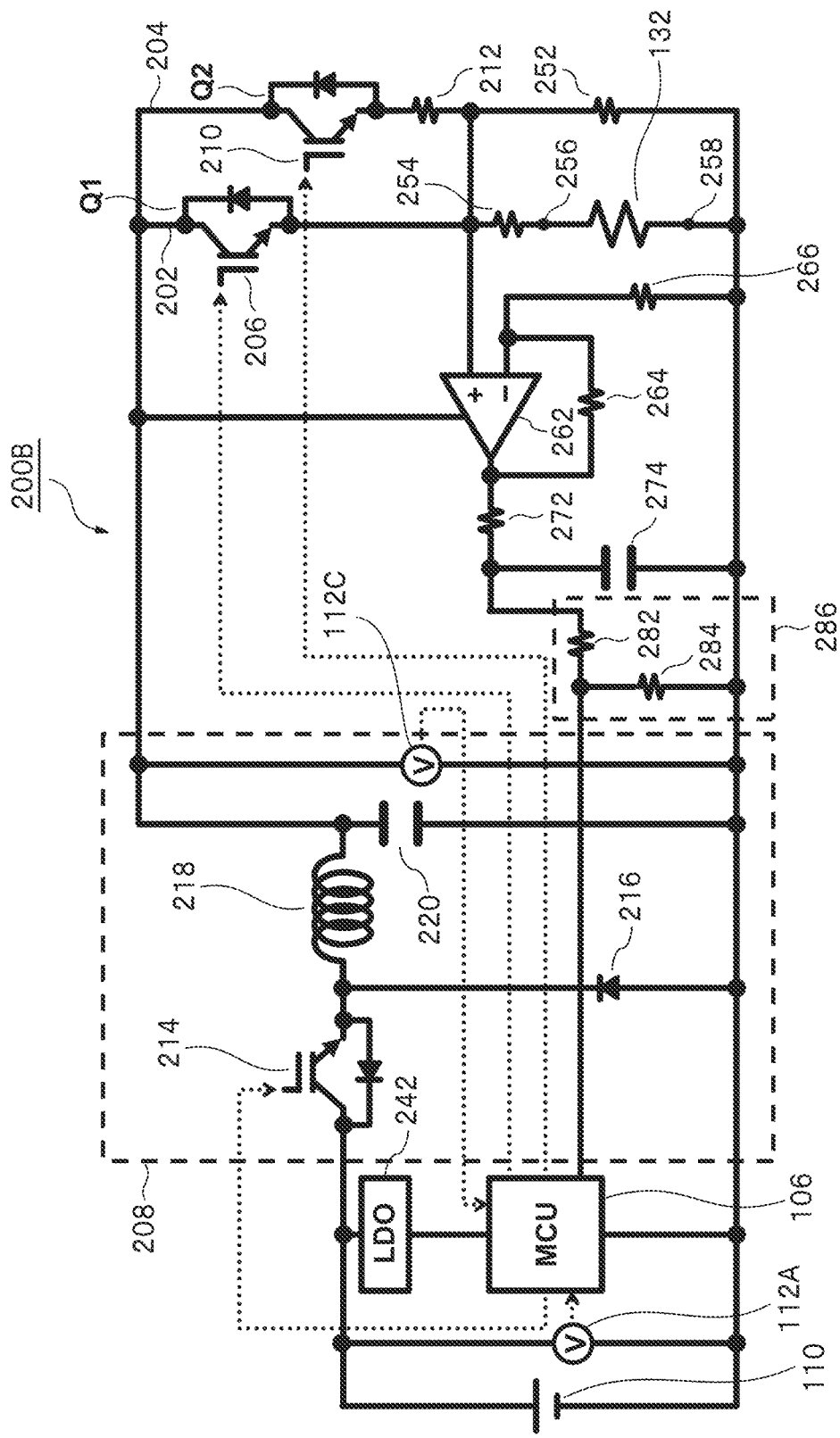

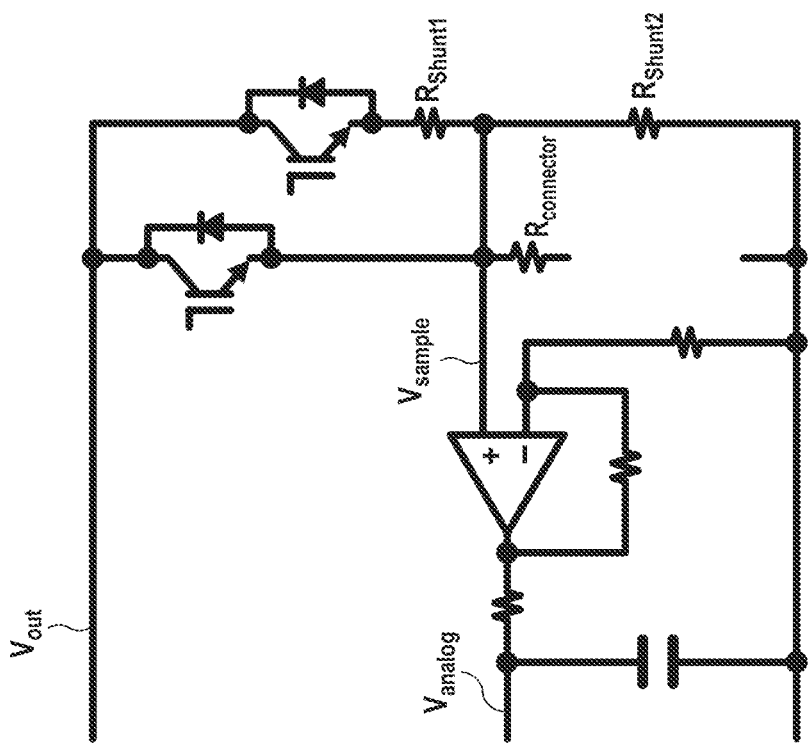
F I G. 3B
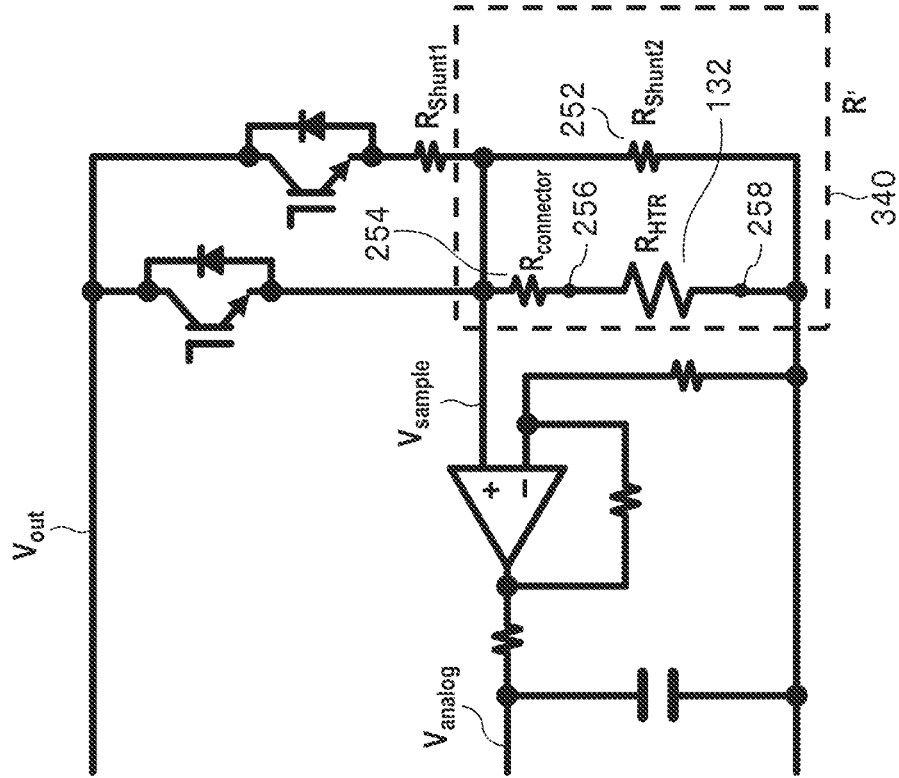
F I G. 3A

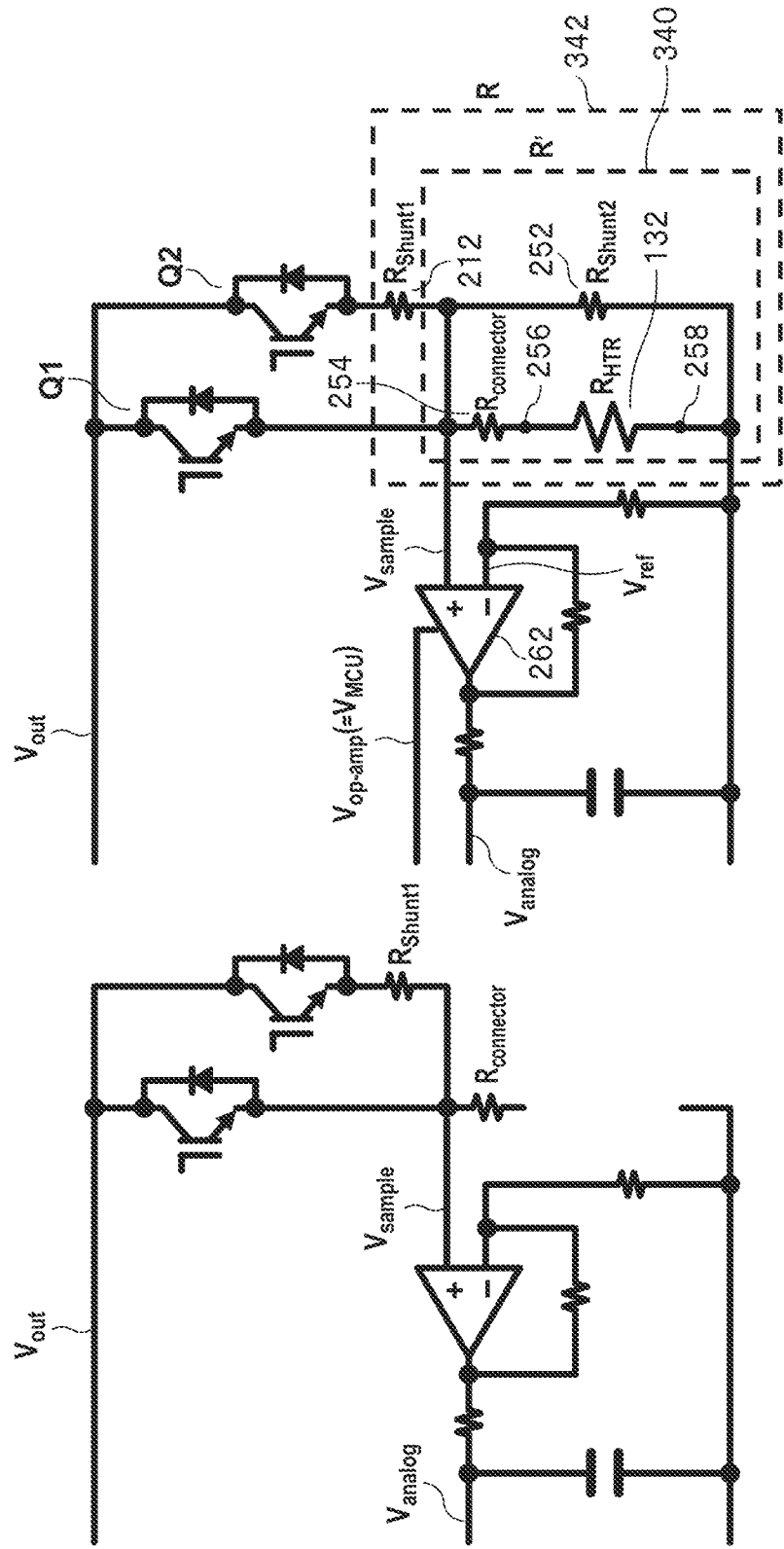

CONTROL DEVICE FOR AEROSOL INHALATION DEVICE AND AEROSOL INHALATION DEVICE

CROSS-REFERENCE TO RELATED APPLICATIONS

This application is a continuation of U.S. application Ser. No. 16/885,337, filed May 28, 2020, which claims priority to and the benefit of Japanese Patent Application No. 2019-102263 filed on May 31, 2019, the entire disclosure of each are incorporated herein by reference.

This application is also related to U.S. patent application Ser. No. 16/885,343, entitled "AEROSOL INHALATION DEVICE AND CONTROL DEVICE FOR AEROSOL INHALATION DEVICE" and U.S. patent application Ser. No. 16/885,393, entitled "CONTROL DEVICE FOR AEROSOL INHALATION DEVICE AND AEROSOL INHALATION DEVICE", all filed on the same day as this application, and all hereby incorporated by reference.

BACKGROUND OF THE INVENTION

Field of the Invention

The present invention relates to a control device for an aerosol inhalation device configured to generate an aerosol to be inhaled by a user and the aerosol suction device. Note that the aerosol inhalation device is also called an aerosol generation device.

Description of the Related Art

In a general aerosol inhalation device such as an electronic cigarette, a heated tobacco product, or a nebulizer, which is used to generate an aerosol to be inhaled by a user, if the user performs inhalation when an aerosol source (to be also referred to as an "aerosol forming substrate" hereinafter) that changes to an aerosol by atomization is in shortage, a sufficient aerosol cannot be supplied to the user. Additionally, in a case of an electronic cigarette or a heated tobacco product, it is impossible to generate an aerosol having an intended flavor.

To detect the remaining amount of an aerosol source, there exists a method using a heater having a PTC characteristic that changes an electrical resistance value in accordance with a temperature. In this method, based on the electrical resistance value of a heater, which is obtained from a voltage applied to the heater or a voltage according to the voltage (to be referred to as "a voltage applied to a heater, or the like" hereinafter), it can be determined whether the aerosol source is in shortage.

There also exists an aerosol inhalation device configured to exchange a cartridge including an aerosol source and a heater that heats the aerosol source when the aerosol source has run out. The exchange can also be detected by the method using the voltage applied to the heater, or the like.

That is, in the aerosol inhalation device, processing based on the voltage applied to the heater, or the like is sometimes executed. To execute the processing based on the voltage applied to the heater, or the like, a control device for the aerosol inhalation device can include an operational amplifier configured to output a voltage according to the voltage applied to the heater, and a control unit such as a microcontroller unit (MCU) to which a voltage according to the voltage is applied. In such a control device, the operational amplifier or the control unit may not normally operate due to an excessive voltage (to be referred to as an "overvoltage" hereinafter) if the operational amplifier or the control unit is not protected from the relatively high voltage applied to the heater.

PTL 1 discloses a circuit arrangement used to control the coil temperature of a resistance heating element of a vaporizing device. This circuit arrangement includes a battery BATT (23), a resistor R_COIL (74) of a coil to which a voltage from the battery BATT (23) can be applied, and an MCU (72) that is connected to the resistor R_COIL (74) of the coil and uses the voltage of the battery BATT (23) as a power supply voltage (see paragraph 0191 and FIG. 17B and the like). However, PTL 1 neither discloses nor suggests an arrangement that prevents an overvoltage from being applied to an operational amplifier or the MCU (72).

PTL 2 discloses a circuit arrangement for measuring the resistance of a heating element of an aerosol generation system. This circuit arrangement includes a heater 501, and a microprocessor 507 connected to the heater 501, to which a voltage V1 can be applied (see paragraph 0081 and FIG. 5 and the like). However, PTL 2 neither discloses nor suggests an arrangement that prevents an overvoltage from being applied to an operational amplifier or the microprocessor 507.

PTL 3 discloses a principle block diagram of a battery assembly of an electronic cigarette. This block diagram includes a battery assembly 101, a spraying assembly 20 connected to the battery assembly 101, and a microcontroller 102 connected to the battery assembly 101 and the spraying assembly 20 (see paragraph 0021 and FIG. 2 and the like). However, PTL 3 neither discloses nor suggests an arrangement that prevents an overvoltage from being applied to an operational amplifier or the microcontroller 102.

PTL 4 discloses a control body 102 and a cartridge 104 of an aerosol sending device. The cartridge 104 includes a heater 222, and the control body 102 includes a microprocessor 310 which is electrically connected to the heater 222 when the cartridge 104 is connected, and to which a voltage V is applied (see paragraph 0064 and FIG. 3 and the like). However, PTL 4 neither discloses nor suggests an arrangement that prevents an overvoltage from being applied to an operational amplifier or the microprocessor 310.

PATENT LITERATURES

PTL 1: Japanese PCT National Publication No. 2017-501805
PTL 2: Japanese PCT National Publication No. 2014-501105
PTL 3: Japanese PCT National Publication No. 2017-503520
PTL 4: Japanese PCT National Publication No. 2018-526983

SUMMARY OF THE INVENTION

The present invention has been made in consideration of the above-described points.

The first problem to be solved by the present invention is to provide a control device for an aerosol inhalation device, which includes an operational amplifier and the like, in which the voltage of a circuit electrically connected to the noninverting input terminal or the inverting input terminal of the operational amplifier is relatively high, and which can prevent an overvoltage from being applied to the operational amplifier or the like.

The second problem to be solved by the present invention is to provide a control device for an aerosol inhalation device, which includes a control unit electrically connected to the output terminal of an operational amplifier, and can prevent an overvoltage higher than the power supply voltage of the control unit from being applied to the control unit.

In order to solve the above-described first problem, according to the embodiment of the present invention, there is provided a control device for an aerosol inhalation device, comprising an operational amplifier configured to perform output according to a voltage applied to a load configured to heat an aerosol source and having a correlation between a temperature and an electrical resistance value, a control unit configured to perform processing based on the voltage according to the output, and a diode having an anode electrically connected to one of an inverting input terminal and a noninverting input terminal of the operational amplifier.

The control device for the aerosol inhalation device according to the embodiment may further comprise a circuit configured to electrically connect a power supply and the load, the circuit may be formed by a first region, and a second region in which a maximum voltage is lower than a maximum voltage in the first region, or an applied voltage is lower than a voltage applied to the first region, and of the inverting input terminal and the noninverting input terminal, a terminal to which the anode of the diode is electrically connected may electrically be connected to the first region.

In the embodiment, the anode of the diode may electrically be connected to the first region.

According to this arrangement, a forward current flows to the diode, thereby preventing an overvoltage from being applied to the input terminal of the operational amplifier. Hence, it is possible to prevent an operation error of the operational amplifier or the like, which is caused by application of an overvoltage to the input terminal.

In the embodiment, the load may electrically be connected to or included in the first region.

According to the arrangement, a relatively high voltage can be applied to the load, for example, a heater, and an aerosol can be generated more efficiently.

The control device for the aerosol inhalation device according to the embodiment may further comprise a converter configured to output a predetermined voltage to be applied to the first region.

In the embodiment, the converter may comprise a switching regulator.

According to the arrangement, the voltage can stably be applied to the load, for example, a heater independently of the remaining amount or degradation state of the power supply, and therefore, aerosol generation can be controlled more stably.

In the embodiment, the converter may further be configured to output a voltage that prevents a forward current flowing to the diode from exceeding an allowable value and allows the load to generate an aerosol.

According to the arrangement, an overcurrent can be prevented from flowing to the diode, and an aerosol can be generated. It is therefore possible to simultaneously solve conflicting problems, that is, generation of a sufficient aerosol and protection of the diode.

In the embodiment, the converter may further be configured to be able to output a plurality of voltages or voltages in a range, the voltages preventing a forward current flowing to the diode from exceeding an allowable value and allowing the load to generate an aerosol.

In the embodiment, the control unit may be configured to adjust an output voltage of the converter in the plurality of voltages or the voltages in the range in accordance with a type of the load.

According to the arrangement, an appropriate voltage can be used in accordance with the type of the load, and it is therefore possible to implement an aerosol inhalation device capable of using various kinds of loads using a single control device.

In the embodiment, a power supply terminal of the operational amplifier may electrically be connected to the second region.

According to the arrangement, a forward current flows to the diode, thereby preventing an overvoltage from being applied to the input terminal of the operational amplifier. Hence, it is possible to prevent an operation error of the operational amplifier or the like, which is caused by application of an overvoltage to the input terminal.

The control device for the aerosol inhalation device according to the embodiment may further comprise a regulator configured to output a voltage to be applied to the second region, and the control unit may be configured such that a power supply terminal of the control unit is electrically connected to the second region.

According to the arrangement, an appropriate voltage can be applied by the regulator to the control unit that is driven by a relatively low voltage. At the same time, since the voltage in the second region is stabilized by the regulator, power can be released to the second region via the diode at the time of overvoltage generation in the inverting input terminal or the noninverting input terminal of the operational amplifier.

In the embodiment, a cathode of the diode may electrically be connected to the second region.

In the embodiment, an electrical resistance value of the diode in a forward direction may be smaller than an electrical resistance value of the operational amplifier.

In the embodiment, a cathode of the diode may electrically be connected to a power supply terminal of the operational amplifier, or a potential at the cathode of the diode may equal a potential at the power supply terminal of the operational amplifier.

According to the arrangement, a forward current flows to the diode, thereby preventing an overvoltage from being applied to the input terminal of the operational amplifier. Hence, it is possible to prevent an operation error of the operational amplifier or the like, which is caused by application of an overvoltage to the input terminal.

The control device for the aerosol inhalation device according to the embodiment further comprises a first circuit and a second circuit, which are electrically connected in parallel between a power supply and the load, the first circuit and the second circuit including a first switch and a second switch, respectively, and being configured such that an electrical resistance value of the second circuit is higher than an electrical resistance value of the first circuit, and the control unit may further be configured to acquire the voltage according to the output of the operational amplifier during a time when the second switch is in an ON state.

According to the arrangement, since a dedicated circuit used to acquire a voltage, which includes a known resistor, is provided, the acquisition accuracy is improved by the known resistor. Simultaneously, it is possible to generate an aerosol without any influence of the known resistor. This improves the use efficiency of the storage capacity of the power supply, for example, a lithium ion secondary battery.

In the embodiment, the control unit may be configured to set the first switch in the ON state to generate an aerosol.

According to the arrangement, power can be supplied to the load without any influence of the electrical resistance value of the second circuit, and it is therefore possible to efficiently generate an aerosol. In other words, a large amount of aerosol can be generated by one charge.

The control device for the aerosol inhalation device according to the embodiment further comprises the load electrically connected in series with the first circuit and the second circuit, and a second resistor electrically connected in series with the first circuit and the second circuit and electrically connected in parallel with the load, and the load may be configured to be detachable from the first circuit, the second circuit, and the second resistor.

In the embodiment, the second circuit may include a first resistor, and an electrical resistance value of the first resistor and an electrical resistance value of the second resistor may equal.

According to the arrangement, even if the load is detached, an electrical path via the second resistor exists. Hence, since the operational amplifier can perform an output according to the voltage applied to the second resistor, the output is stable.

Also, in order to solve the above-described first problem, according to the embodiment of the present invention, there is provided a control device for an aerosol inhalation device, comprising a comparator configured to perform output according to a voltage applied to a load configured to heat an aerosol source and having a correlation between a temperature and an electrical resistance value, a control unit configured to perform processing based on the voltage according to the output, and a diode having an anode electrically connected to an input terminal of the comparator.

According to the arrangement, a forward current flows to the diode, thereby preventing an overvoltage from being applied to the input terminal of the comparator. Hence, it is possible to prevent an operation error of the comparator or the like, which is caused by application of an overvoltage to the input terminal.

Furthermore, in order to solve the above-described first problem, according to the embodiment of the present invention, there is provided a control device for an aerosol inhalation device, comprising an operational amplifier configured to perform output according to a voltage applied to a load configured to heat an aerosol source and having a correlation between a temperature and an electrical resistance value, a control unit configured to perform processing based on the voltage according to the output, and an aerosol generation circuit including the load, wherein a power supply voltage of the operational amplifier equals a voltage applied to the aerosol generation circuit, and one of an inverting input terminal and a noninverting input terminal of the operational amplifier is electrically connected to the aerosol generation circuit.

According to the arrangement, since the voltage applied to the inverting input terminal or the noninverting input terminal of the operational amplifier is equal to or lower than the power supply voltage of the operational amplifier. Hence, it is possible to prevent an operation error of the operational amplifier or the like, which is caused by application of an overvoltage to the operational amplifier.

Furthermore, in order to solve the above-described first problem, according to the embodiment of the present invention, there is provided an aerosol inhalation device comprising a control device as described above.

According to the arrangement, a forward current flows to the diode, thereby preventing an overvoltage from being applied to the input terminal of the operational amplifier or the comparator. Hence, it is possible to prevent an operation error of the operational amplifier or the comparator or the like, which is caused by application of an overvoltage to the input terminal.

Alternatively, according to the arrangement, since the voltage applied to the inverting input terminal or the non-inverting input terminal of the operational amplifier is equal to or lower than the power supply voltage of the operational amplifier. Hence, it is possible to prevent an operation error of the operational amplifier or the like, which is caused by application of an overvoltage to the operational amplifier.

In order to solve the above-described second problem, according to the embodiment of the present invention, there is provided a control device for an aerosol inhalation device, comprising an operational amplifier including an output terminal configured to generate a voltage according to a voltage applied to a load configured to heat an aerosol source and having a correlation between a temperature and an electrical resistance value, a control unit including an input terminal and configured to perform processing based on a voltage applied to the input terminal, and a voltage dividing circuit configured to electrically connect the output terminal of the operational amplifier and the input terminal of the control unit.

In the embodiment, the voltage dividing circuit may be configured such that the voltage applied to the input terminal of the control unit becomes not more than a power supply voltage of the control unit.

In the embodiment, a power supply voltage of the operational amplifier may be higher than the power supply voltage of the control unit.

According to the arrangement, a voltage stepped down by the voltage dividing circuit is applied to the input terminal of the control unit. This can prevent an operation error of the control unit or the like, which is caused by application of an overvoltage to the input terminal.

In the embodiment, an amplification factor of the operational amplifier may be set such that the voltage applied to the input terminal of the control unit becomes not more than the power supply voltage of the control unit.

According to the arrangement, an overvoltage is not applied to the input terminal of the control unit. This can prevent an operation error of the control unit or the like, which is caused by application of an overvoltage to the input terminal.

In the embodiment, a power supply voltage of the operational amplifier may equal a voltage applied to an aerosol generation circuit including the load, and one of an inverting input terminal and a noninverting input terminal of the operational amplifier may electrically be connected to the aerosol generation circuit.

According to the arrangement, a voltage higher than the power supply voltage of the operational amplifier is not applied to the input terminal of the operational amplifier. Hence, it is possible to prevent an operation error of the operational amplifier or the like, which is caused by application of an overvoltage to the input terminal.

The control device for the aerosol inhalation device according to the embodiment may further comprise a converter configured to apply a predetermined voltage to an aerosol generation circuit including the load.

In the embodiment, an output terminal of the converter may electrically be connected to the aerosol generation circuit and a power supply terminal of the operational amplifier, and one of an inverting input terminal and a noninverting input terminal of the operational amplifier may electrically be connected to the aerosol generation circuit.

According to the arrangement, the voltage can stably be applied to the load, for example, a heater, and therefore, aerosol generation can be controlled more accurately.

In the embodiment, the converter may be configured to output a voltage that makes the voltage applied to the input terminal of the control unit not more than a power supply voltage of the control unit and allows the load to generate an aerosol.

In the embodiment, the voltage dividing circuit may be configured such that the voltage applied to the input terminal of the control unit becomes not more than the power supply voltage of the control unit.

According to the arrangement, it is possible to prevent an overvoltage from being applied to the input terminal of the control unit and also generate an aerosol. It is therefore possible to prevent an operation error of the control unit or the like during aerosol generation.

In the embodiment, the converter may comprise a switching regulator.

According to the arrangement, the voltage can stably be applied to the load, for example, a heater, and therefore, aerosol generation can be controlled more accurately.

In the embodiment, the converter may be configured to be able to output a plurality of voltages or voltages in a range, the voltages making the voltage applied to the input terminal of the control unit not more than a power supply voltage of the control unit and allowing the load to generate an aerosol.

In the embodiment, the control unit may be configured to adjust an output voltage of the converter in accordance with a type of the load.

According to the arrangement, an appropriate voltage can be used in accordance with the type of the load, and it is therefore possible to implement an aerosol inhalation device capable of using various kinds of loads using a single control device.

The control device for the aerosol inhalation device according to the embodiment further comprises a first circuit and a second circuit, which are electrically connected in parallel between a power supply and the load, the first circuit and the second circuit including a first switch and a second switch, respectively, and being configured such that an electrical resistance value of the second circuit is larger than an electrical resistance value of the first circuit, and the control unit may further be configured to acquire the voltage applied to the input terminal during a time when the second switch is in an ON state.

According to the arrangement, since a dedicated circuit used to acquire a voltage, which includes a known resistor, is provided, the acquisition accuracy is improved by the known resistor. Simultaneously, it is possible to generate an aerosol without any influence of the known resistor. This improves the use efficiency of the storage capacity of the power supply, for example, a lithium ion secondary battery.

In the embodiment, the control unit may be configured to set the first switch in the ON state to generate an aerosol.

According to the arrangement, power can be supplied to the load without any influence of the electrical resistance value of the second circuit, and it is therefore possible to efficiently generate an aerosol.

The control device for the aerosol inhalation device according to the embodiment may further comprise the load electrically connected in series with the first circuit and the second circuit, and a second resistor electrically connected in series with the first circuit and the second circuit and electrically connected in parallel with the load, and the load may be configured to be detachable from the first circuit, the second circuit, and the second resistor.

In the embodiment, the second circuit may include a first resistor, and an electrical resistance value of the first resistor and an electrical resistance value of the second resistor may equal.

According to the arrangement, even if the load is detached, an electrical path via the second resistor exists. Hence, since the operational amplifier can perform an output according to the voltage applied to the second resistor, the output is stable.

Furthermore, in order to solve the above-described second problem, according to the embodiment of the present invention, there is provided an aerosol inhalation device comprising a control device as described above.

According to the arrangement, a voltage stepped down by the voltage dividing circuit is applied to the input terminal of the control unit. This can prevent an operation error of the control unit or the like, which is caused by application of an overvoltage to the input terminal.

Further features of the present invention will become apparent from the following description of exemplary embodiments (with reference to the attached drawings).

BRIEF DESCRIPTION OF THE DRAWINGS

FIG. 1A is a schematic block diagram of an exemplary arrangement of an aerosol inhalation device according to an embodiment of the present invention;

FIG. 1B is a schematic block diagram of another exemplary arrangement of the aerosol inhalation device according to the embodiment of the present invention;

FIG. 2A is a circuit diagram showing the circuit arrangement of an exemplary control device for the aerosol inhalation device according to the embodiment of the present invention;

FIG. 2B is a circuit diagram showing the circuit arrangement of the exemplary control device for the aerosol inhalation device according to the embodiment of the present invention;

FIG. 2C is a circuit diagram showing the circuit arrangement of another exemplary control device for the aerosol inhalation device according to the embodiment of the present invention;

FIG. 2D is a circuit diagram showing the circuit arrangement of another exemplary control device for the aerosol inhalation device according to the embodiment of the present invention;

FIG. 3A is a circuit diagram showing some circuits of the exemplary control device when a load is attached;

FIG. 3B is a circuit diagram showing some circuits of the exemplary control device when a load is detached;

FIG. 3C is a circuit diagram showing some circuits of the exemplary control device when a load is detached, for which a second shunt resistor is assumed to be absent;

FIG. 3D is a circuit diagram showing some circuits of the exemplary control device, for which a diode electrically connected to an operational amplifier is assumed to be absent;

FIG. 3E is a circuit diagram showing an equivalent circuit of a constituent element of some circuits of the exemplary control device;

Figure 5:
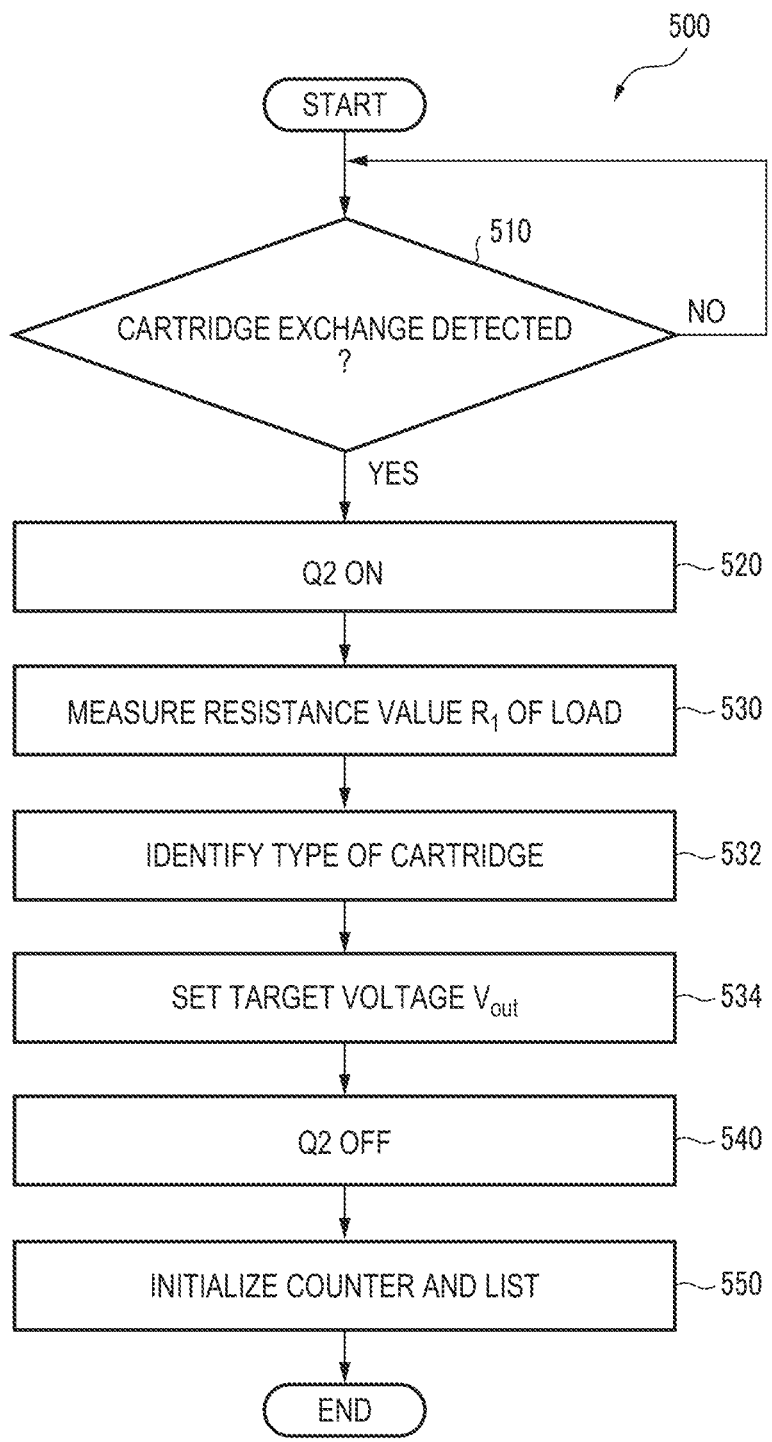

FIGS. 4A, 4A-2 and 4B show a flowchart of exemplary main processing for measuring the temperature of a load and judging exhaustion or shortage of an aerosol source; and FIG. 5 is a flowchart of exemplary processing for supporting main processing.

DESCRIPTION OF THE EMBODIMENTS

An embodiment of the present invention will now be described in detail with reference to the accompanying drawings. Note that the embodiment of the present invention includes an electronic cigarette, a heated tobacco product, and a nebulizer, but is not limited to these. The embodiment of the present invention can include various aerosol inhalation devices configured to generate an aerosol to be inhaled by a user.

1 OUTLINE OF AEROSOL INHALATION DEVICE

FIG. 1A is a schematic block diagram of the arrangement of an aerosol inhalation device 100A according to an embodiment of the present invention. FIG. 1A schematically and conceptionally shows components provided in the aerosol inhalation device 100A but does not show the strict arrangement, shapes, dimensions, positional relationship, and the like of the components and the aerosol inhalation device 100A.

As shown in FIG. 1A, the aerosol inhalation device 100A includes a first member 102 (to be referred to as a "main body 102" hereinafter), and a second member 104A (to be referred to as a "cartridge 104A" hereinafter). As shown in FIG. 1A, as an example, the main body 102 may include a control unit 106, a notification unit 108, a power supply 110, a sensor 112, and a memory 114. The aerosol inhalation device 100A may include sensors such as a flow velocity sensor, a flow rate sensor, a pressure sensor, a voltage sensor, a current sensor, and a temperature sensor. In the present invention, these will also collectively be referred to as the "sensor 112". The main body 102 may also include a circuit 134 to be described later. As an example, the cartridge 104A may include a storage unit 116A, an atomization unit 118A, an air intake channel 120, an aerosol channel 121, a mouthpiece portion 122, a holding portion 130, and a load 132. Some of the components included in the main body 102 may be included in the cartridge 104A. Some of the components included in the cartridge 104A may be included in the main body 102. The cartridge 104A may be configured to be detachable from the main body 102. Alternatively, all the components included in the main body 102 and the cartridge 104A may be included in a single housing in place of the main body 102 and the cartridge 104A.

The storage unit 116A may be formed as a tank to store an aerosol source. In this case, the aerosol source is, for example, a polyhydric alcohol such as glycerol or propylene, a liquid such as water, or a liquid mixture thereof. If the aerosol inhalation device 100A is an electronic cigarette, the aerosol source in the storage unit 116A may contain a component that discharges a flavor component when heated. The holding portion 130 holds the aerosol source supplied from the storage unit 116A at a position where the load 132 can heat. For example, the holding portion 130 is made of a fibrous or porous material and holds an aerosol source as a liquid in gaps between fibers or in the pores of the porous material. As the above-described fibrous or porous material, for example, cotton, glass fiber, a tobacco raw material, or the like can be used. If the aerosol inhalation device 100A is a medical inhalation device such as a nebulizer, the aerosol source may also contain a drug to be inhaled by a patient. As another example, the storage unit 116A may include a component capable of replenishing the consumed aerosol source. Alternatively, the storage unit 116A may be configured such that the storage unit 116A itself can be exchanged when the aerosol source is consumed. The aerosol source is not limited to a liquid and may be a solid. If the aerosol source is a solid, the storage unit 116A may be a hollow container.

The atomization unit 118A is configured to atomize the aerosol source and generate an aerosol. If an inhalation operation or another operation by the user is detected by the sensor 112, the atomization unit 118A generates an aerosol. For example, the holding portion 130 is provided to connect the storage unit 116A and the atomization unit 118A. In this case, a part of the holding portion 130 communicates with the inside of the storage unit 116A and contacts the aerosol source. Another part of the holding portion 130 extends to the atomization unit 118A. Note that the other part of the holding portion 130 extending to the atomization unit 118A may be stored in the atomization unit 118A, or may communicate with the inside of the storage unit 116A via the atomization unit 118A. The aerosol source is carried from the storage unit 116A to the atomization unit 118A by the capillary effect of the holding portion 130. As an example, the atomization unit 118A includes a heater including the load 132 electrically connected to the power supply 110. Note that in the present application, "electrically connected" may indicates a state in which electricity can be transported between two elements electrically connected to each other. If electricity can be transported between two elements, the method can be either wired or wireless. Hence, a third element, for example, a resistor may be included between the two electrically connected elements or not. The heater is arranged in contact with or in proximity of the holding portion 130. If an inhalation operation or another operation by the user is detected by the sensor 112, the control unit 106 controls power supply to the heater of the atomization unit 118A and heats the aerosol source carried via the holding portion 130, thereby atomizing the aerosol source. The air intake channel 120 is connected to the atomization unit 118A, and the air intake channel 120 communicates with the outside of the aerosol inhalation device 100A. The aerosol generated by the atomization unit 118A is mixed with air taken via the air intake channel 120. The fluid mixture of the aerosol and air is sent to the aerosol channel 121, as indicated by an arrow 124. The aerosol channel 121 has a tubular structure configured to transport the fluid mixture of air and the aerosol generated by the atomization unit 118A to the mouthpiece portion 122.

The mouthpiece portion 122 is located at the end of the aerosol channel 121 and configured to open the aerosol channel 121 to the outside of the aerosol inhalation device 100A. The user holds the mouthpiece portion 122 in the mouth and inhales, thereby taking the air containing the aerosol into the oral cavity.

The notification unit 108 may include a light emitting element such as an LED, a display, a speaker, a vibrator, and the like. The notification unit 108 is configured to make some notification to the user as needed by light emission, display, utterance, vibration, or the like.

Note that the cartridge 104A can be formed as an outer tube, and one or both of the air intake channel 120 and the aerosol channel 121 can be formed as an inner tube arranged in the outer tube. The load 132 can be arranged in the air intake channel 120 or the aerosol channel 121 that is the inner tube. The storage unit 116A can be arranged or formed between the cartridge 104A that is the outer tube and the air intake channel 120 or the aerosol channel 121 that is the inner tube.

The power supply 110 supplies power to the components such as the notification unit 108, the sensor 112, the memory 114, the load 132, and the circuit 134 in the aerosol inhalation device 100A. The power supply 110 may be a primary battery or a secondary battery that can be charged by connecting to an external power supply via a predetermined port (not shown) of the aerosol inhalation device 100A. Only the power supply 110 may be detachable from the main body 102 or the aerosol inhalation device 100A, or may be exchangeable with a new power supply 110. In addition, the power supply 110 may be exchangeable with a new power supply 110 by exchanging the whole main body 102 with a new main body 102. As an example, the power supply 110 may be formed by a lithium ion secondary battery, a nickel hydrogen secondary battery, a lithium ion capacitor, or the like. The power supply 110 that is the secondary battery may include a temperature sensor configured to detect the temperature of the battery.

The sensor 112 may include one or a plurality of sensors used to acquire the value of a voltage applied to the whole or a specific part of the circuit 134, the value of a current flowing to the whole or a specific part of the circuit 134, a value associated with the electrical resistance value of the load 132 or a value associated with the temperature, and the like. The sensor 112 may be incorporated in the circuit 134. The function of the sensor 112 may be incorporated in the control unit 106. The sensor 112 may also include at least one of a pressure sensor that detects a variation in the pressure in one or both of the air intake channel 120 and the aerosol channel 121, a flow velocity sensor that detects a flow velocity, and a flow rate sensor that detects a flow rate. The sensor 112 may also include a weight sensor that detects the weight of a component such as the storage unit 116A. The sensor 112 may also be configured to count the number of puffs by the user who uses the aerosol inhalation device 100A. The sensor 112 may also be configured to integrate the time of energization to the atomization unit 118A. The sensor 112 may also be configured to detect the liquid level in the storage unit 116A. The sensor 112 may also be configured to obtain or detect the SOC (State Of Charge), current integrated value, voltage, and the like of the power supply 110. The SOC may be obtained by the current integration method (coulomb counting method), the SOC-OCV (Open Circuit Voltage) method, or the like. The sensor 112 may also include the above-described temperature sensor in the power supply 110. The sensor 112 may be able to detect an operation for an operation button that can be operated by the user.

The control unit 106 can be an electronic circuit module formed as a microprocessor or a microcomputer, for example, an MPC. The control unit 106 may be configured to control the operation of the aerosol inhalation device 100A in accordance with computer executable instructions stored in the memory 114. The memory 114 is a storage medium such as a ROM, a RAM, or a flash memory. In addition to the computer executable instructions as described above, the memory 114 may store setting data necessary for control of the aerosol inhalation device 100A. For example, the memory 114 may store various data such as a control method (a form such as light emission, utterance, or vibration) of the notification unit 108, values obtained and/or detected by the sensor 112, and the heating history of the atomization unit 118A. The control unit 106 reads out data from the memory 114 as needed and uses it to control the aerosol inhalation device 100A, and stores data in the memory 114 as needed. Note that the memory 114 may be included in the control unit 106.

Figure 1B:
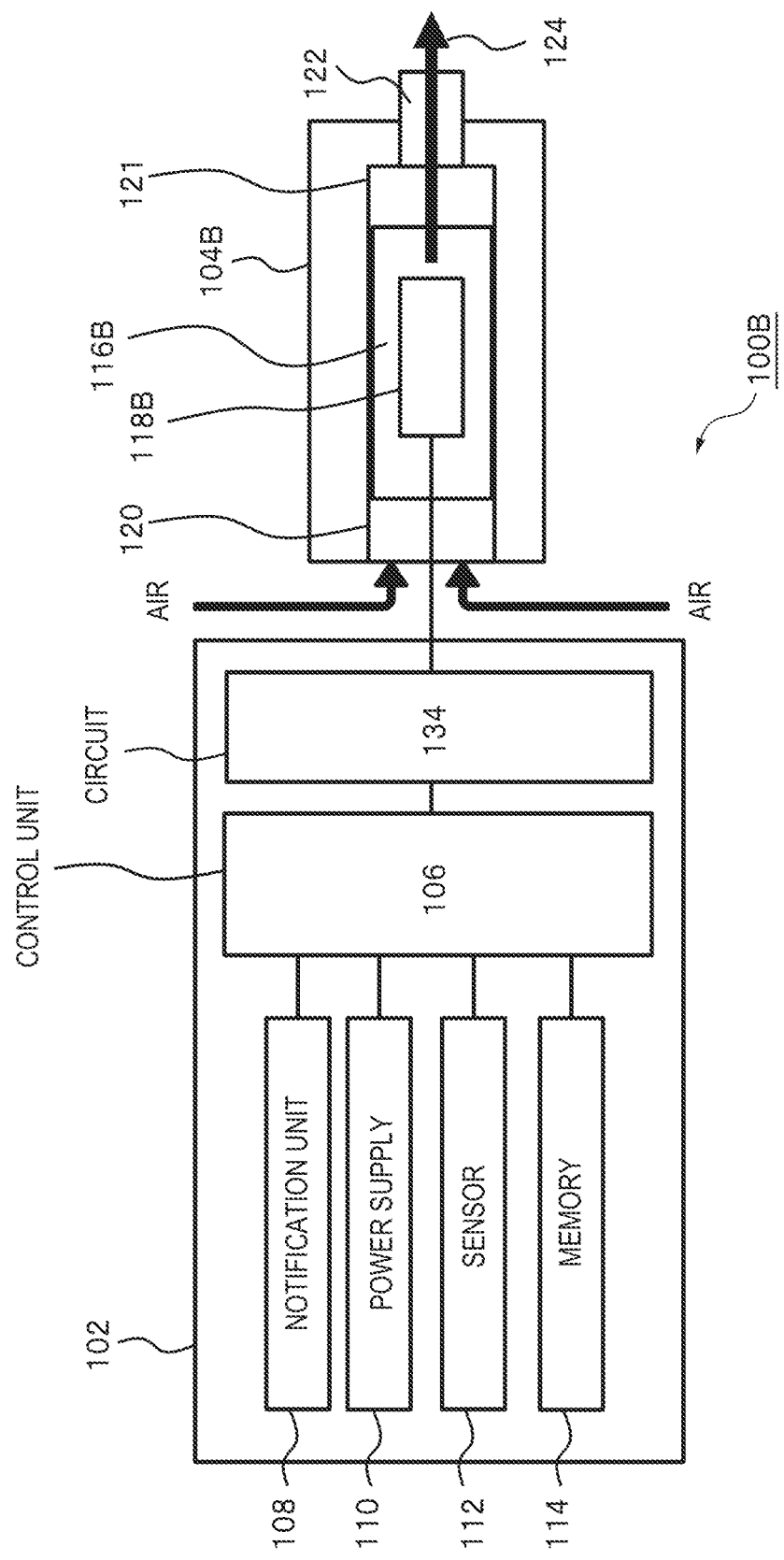

FIG. 1B is a schematic block diagram of the arrangement of an aerosol inhalation device 100B according to the embodiment of the present invention.

As shown in FIG. 1B, the aerosol inhalation device 100B has an arrangement similar to the aerosol inhalation device 100A shown in FIG. 1A. However, the arrangement of the second member 104B (to be referred to as an "aerosol generating article 104B" or "stick 104B" hereinafter) is different from the arrangement of the second member 104A. As an example, the aerosol generating article 104B may include an aerosol base material 116B, an atomization unit 118B, the air intake channel 120, the aerosol channel 121, and the mouthpiece portion 122. Some of the components included in the main body 102 may be included in the aerosol generating article 104B. Some of the components included in the aerosol generating article 104B may be included in the main body 102. The aerosol generating article 104B may be insertable/removable into/from the main body 102. Alternatively, all the components included in the main body 102 and the aerosol generating article 104B may be included in a single housing in place of the main body 102 and the aerosol generating article 104B.

The aerosol base material 116B may be formed as a solid carrying an aerosol source. As in the storage unit 116A shown in FIG. 1A, the aerosol source may be, for example, a polyhydric alcohol such as glycerol or propylene, a liquid such as water, or a liquid mixture thereof. The aerosol source in the aerosol base material 116B may contain a tobacco raw material or an extract derived from a tobacco raw material, which discharges a flavor component when heated. Note that the aerosol base material 116B itself may be made of a tobacco raw material. If the aerosol inhalation device 100B is a medical inhalation device such as a nebulizer, the aerosol source may also contain a drug to be inhaled by a patient. The aerosol base material 116B may be configured such that the aerosol base material 116B itself can be exchanged when the aerosol source is consumed. The aerosol source is not limited to a liquid and may be a solid.

The atomization unit 118B is configured to atomize the aerosol source and generate an aerosol. If an inhalation operation or another operation by the user is detected by the sensor 112, the atomization unit 118B generates an aerosol. The atomization unit 118B includes a heater (not shown) including a load electrically connected to the power supply 110. If an inhalation operation or another operation by the user is detected, the control unit 106 controls power supply to the heater of the atomization unit 118B and heats the aerosol source carried in the aerosol base material 116B, thereby atomizing the aerosol source. The air intake channel 120 is connected to the atomization unit 118B, and the air intake channel 120 communicates with the outside of the aerosol inhalation device 100B. The aerosol generated by the atomization unit 118B is mixed with air taken via the air intake channel 120. The fluid mixture of the aerosol and air is sent to the aerosol channel 121, as indicated by the arrow 124. The aerosol channel 121 has a tubular structure configured to transport the fluid mixture of air and the aerosol generated by the atomization unit 118B to the mouthpiece portion 122.

The control unit 106 is configured to control the aerosol inhalation devices 100A and 100B (to be collectively referred to as the "aerosol inhalation device 100" hereinafter) according to the embodiment of the present invention by various methods.

2 OUTLINE OF CONTROL DEVICE FOR AEROSOL INHALATION DEVICE

2-1 First Control Device
2-1-1 Circuit Arrangement

Figure 2A:
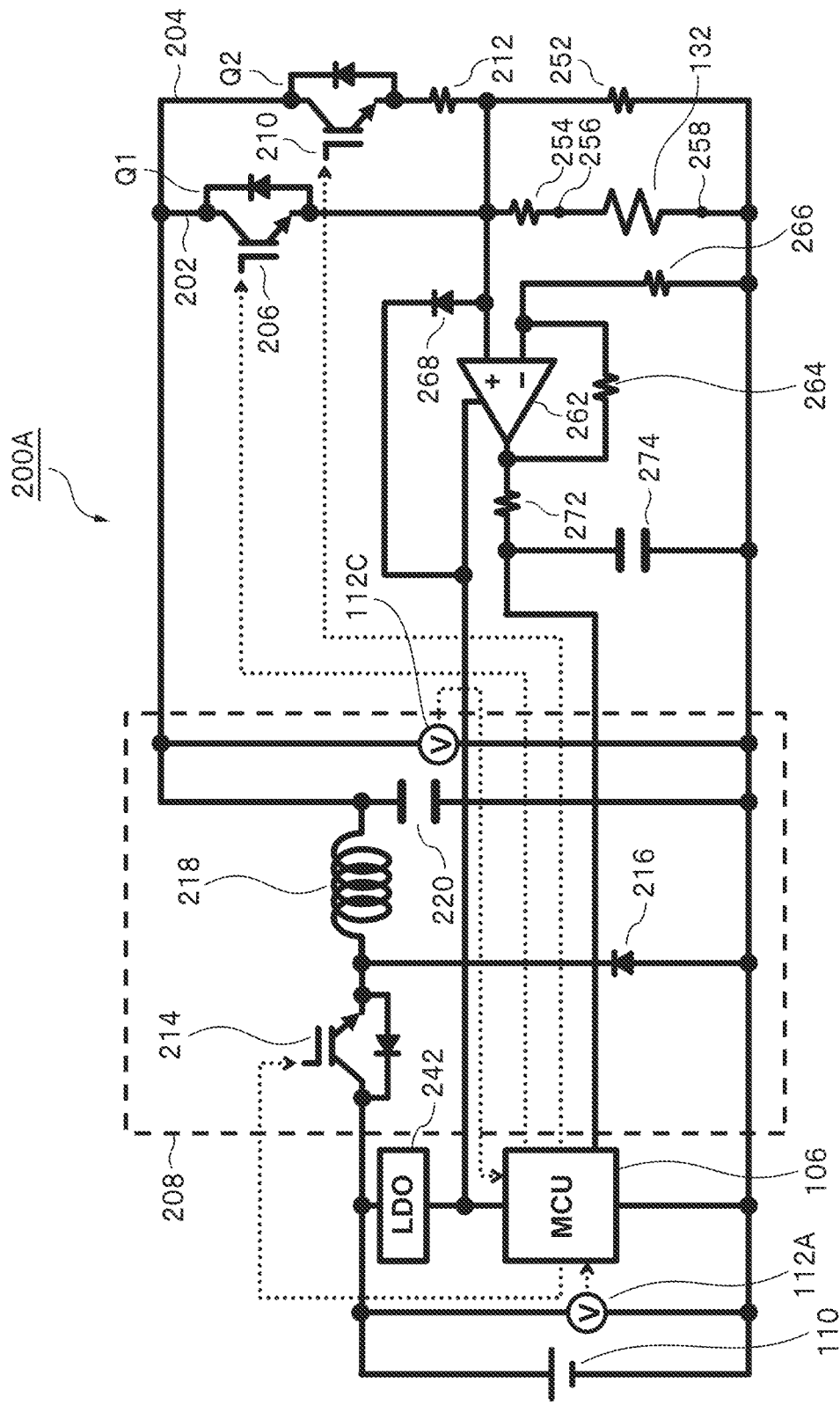
Figure 2B:
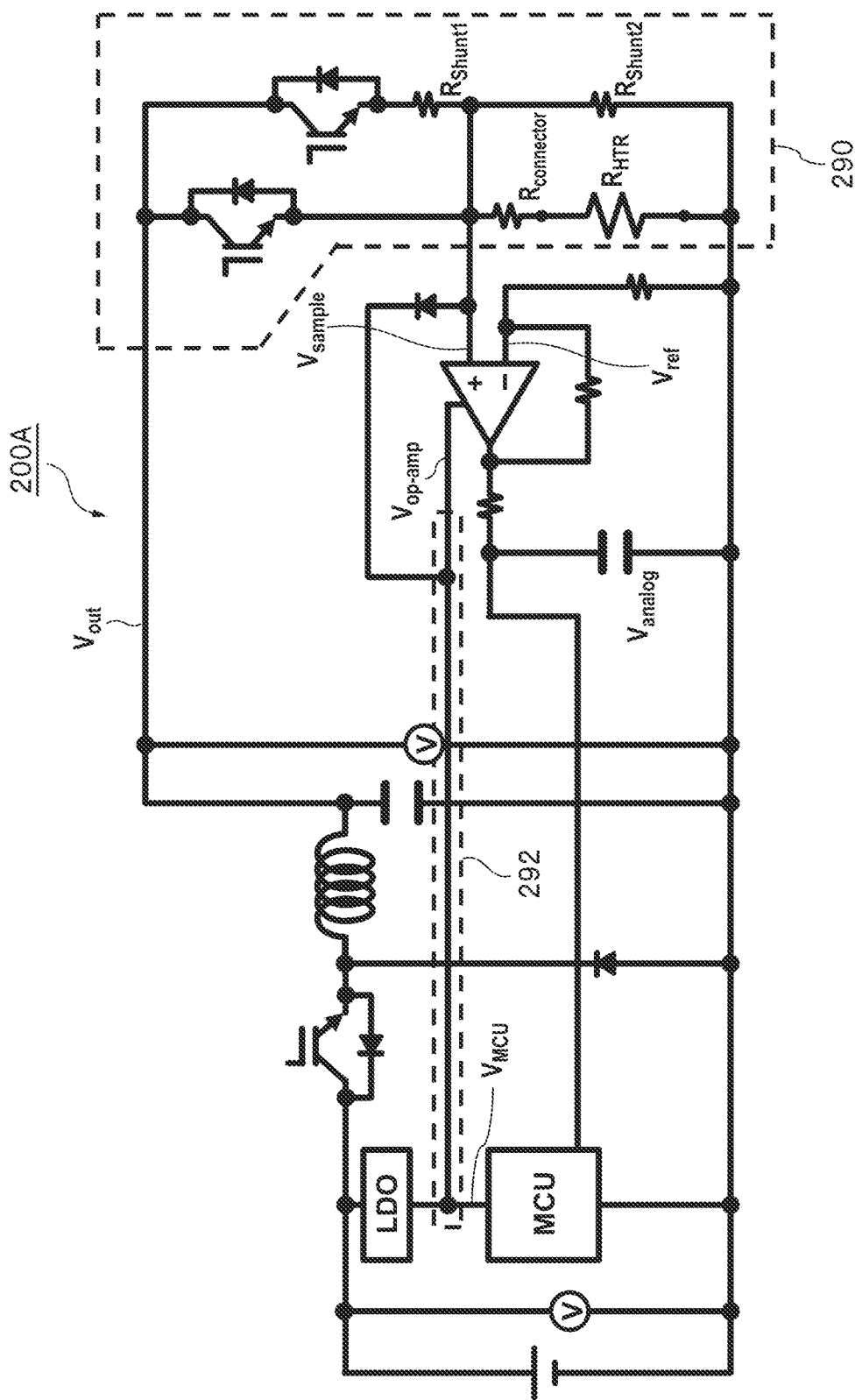

FIGS. 2A and 2B are circuit diagrams showing the schematic circuit arrangement of a control device 200A for the aerosol inhalation device 100 according to the embodiment of the present invention. Reference numerals used to mention the elements of the control device 200A are added in FIG. 2A, and reference symbols and the like concerning voltages and electrical resistance values used in the description are added in FIG. 2B. Note that of the notification unit 108, the power supply 110, the sensor 112, the memory 114, the control unit 106, and the circuit 134, the control device 200A may include elements that are not illustrated.

The control device 200A includes the power supply 110, the MCU that is an example of the control unit 106, a sensor 112A and a sensor 112C, the load 132 (to be also referred to as a "heater resistor" hereinafter, and its electrical resistance value is represented by $R_{HTR}$), a contact resistor 254 (its electrical resistance value is represented by $R_{CONNECTOR}$) of the load 132 in a case in which the load 132 is detachable from the control device 200A, a connection terminal 256 and a connection terminal 258 of the load 132 to circuits, a first circuit 202, a second circuit 204, a switch Q1 including a first field effect transistor (FET) 206, a converter 208 and a regulator 242, a switch Q2 including a second FET 210, a first shunt resistor 212 and a second shunt resistor 252 (their electrical resistance values will be represented by $R_{shunt1}$ and $R_{shunt2}$, respectively, hereinafter), an operational amplifier 262, a resistor 264 and a resistor 266 which are electrically connected to the inverting input terminal of the operational amplifier 262, a diode 268, a resistor 272 electrically connected to the output terminal of the operational amplifier 262, and a capacitor 274 electrically connected to the resistor 272. As for the diode 268, the anode may electrically be connected to the noninverting input terminal of the operational amplifier 262, and the cathode may electrically be connected to the power supply terminal of the operational amplifier 262 (more specifically, it can be a positive-side power supply terminal in a positive-side power supply terminal and a negative-side power supply terminal whose applied voltages are generally referred to as $V_{cc}$ and $V_{EE}$, respectively, and this will also apply to the power supply terminal of the operational amplifier 262 hereinafter). In other words, the potential at the cathode of the diode 268 may equal the potential at the power supply terminal of the operational amplifier 262.

In the control device 200A, $V_{out}$ corresponds to the output voltage of the converter 208, $V_{sample}$ corresponds to a voltage applied to the noninverting input terminal of the operational amplifier 262, $V_{ref}$ corresponds to a voltage applied to the inverting input terminal of the operational amplifier 262, $V_{analog}$ corresponds to a voltage according to the voltage of the output terminal of the operational amplifier 262, which is a voltage applied to the control unit 106, $V_{op-amp}$ corresponds to a voltage applied to the power supply terminal of the operational amplifier 262, that is, the power supply voltage of the operational amplifier 262, and $V_{MCU}$ corresponds to the output voltage of the regulator 242, which is a voltage applied to the power supply terminal of the control unit 106, that is, the power supply voltage of the control unit 106. In the control device 200A, $V_{op-amp}$ equals $V_{MCU}$.

The electrical resistance value of the load 132 changes in accordance with the temperature. In other words, the load 132 can include a PTC heater. Since the electrical resistance value of the load 132 changes in accordance with the temperature, it can be said that the temperature of the load 132 and the electrical resistance value of the load 132 have a correlation. The load 132 is detachably electrically connected to the circuits of the control device 200A via the connection terminal 256 and the connection terminal 258. The load 132 may be included in the control device 200A or not.

The first shunt resistor 212 is electrically connected in series with the load 132 and has the known electrical resistance value $R_{shunt1}$. The electrical resistance value $R_{shunt1}$ of the first shunt resistor 212 can be almost or completely invariable with respect to the temperature. The first shunt resistor 212 has an electrical resistance value larger than that of the load 132. The second shunt resistor 252 can have the same characteristic as the first shunt resistor 212, but is not limited to this. Note that the second shunt resistor 252 is electrically connected in series with the first shunt resistor 212. In addition, the second shunt resistor 252 is electrically connected in parallel with the load 132.

The sensor 112A and the sensor 112C form a part of the sensor 112. The sensor 112A and the sensor 112C may be omitted in accordance with the embodiment.

The first FET 206 included in the switch Q1 and the second FET 210 included in the switch Q2 each play a role of a switch that opens/closes an electrical circuit. It would be obvious for those skilled in the art that as the switch, not only an FET but also various elements such as an IGBT and a contactor can be used to form the switches Q1 and Q2. In addition, the switches Q1 and Q2 preferably have the same characteristic, but may not. Hence, the FETs, IGBTs, contactors, or the like used as the switches Q1 and Q2 preferably have the same characteristic, but may not. Note that if elements having the same characteristic are employed as the switches Q1 and Q2, the procurement cost for each of the switches Q1 and Q2 can be reduced. This makes it possible to manufacture the control device 200A at a lower cost.

The converter 208 can be a DC/DC converter. The converter 208 is, for example, a switching regulator, and can include an FET 214, a diode 216, an inductor 218, and a capacitor 220. The control unit 106 may control the converter 208 such that the converter 208 converts the output voltage of the power supply 110, and the converted output voltage becomes $V_{out}$. Here, the converter 208 is preferably configured to output a predetermined voltage under the control of the control unit 106 during the time when at least the switch Q2 is in an ON state. In addition, the converter 208 may be configured to output a predetermined voltage under the control of the control unit 106 during the time when the switch Q1 is in an ON state as well. Note that in this case, the voltage output by the converter 208 need not strictly be constant. If the target voltage of the converter 208 is maintained constant for a predetermined period, it can be said that the converter 208 is configured to output a predetermined voltage. Note that the predetermined voltage output by the converter 208 under the control of the control unit 106 during the ON state of the switch Q1 and the predetermined voltage output by the converter 208 under the control of the control unit 106 during the ON state of the switch Q2 may be equal or different. If these are different, the predetermined voltage output by the converter 208 under the control of the control unit 106 during the ON state of the switch Q1 may be higher or lower than the predetermined voltage output by the converter 208 under the control of the control unit 106 during the ON state of the switch Q2. According to this arrangement, since the voltages and other parameters are stable, the remaining aerosol amount detection accuracy improves. Furthermore, when a switching regulator is used as the converter 208, a loss generated when a voltage input to the converter 208 is converted into a predetermined voltage can be made small. This can generate a larger amount of aerosol by one charge while improving the remaining aerosol amount detection accuracy.

The converter 208 may be configured to directly apply the output voltage of the power supply 110 to the first circuit 202 under the control of the control unit 106 during the time when only the switch Q1 is in the ON state. This form may be implemented by the control unit 106 controlling the switching regulator 208 in a direct connection mode in which the switching operation stops. Note that the converter 208 is not an essential component but may be omitted. The converter 208 may be of a step-down type shown in FIG. 2A, or may be of a boost type or a step-down/boost type.

Note that the control of the converter 208 may be done by another control unit other than the control unit 106. The other control unit may be provided in the converter 208. In this case, a value detected by the sensor 112C is input at least to the other control unit. Note that in this case as well, a value detected by the sensor 112C may be input to the control unit 106.

The regulator 242 can be, for example, a linear regulator and, more particularly, an LDO (Low Drop-Out Regulator). The regulator 242 is electrically connected to the power supply terminal of the control unit 106, and generates the voltage $V_{MCU}$ used to drive the control unit 106.

The voltage $V_{MCU}$ is a voltage used to drive the control unit 106 and can therefore be a relatively low voltage. On the other hand, the voltage $V_{out}$ is associated with a voltage applied to the load 132, and is preferably a relatively high voltage to improve the atomization efficiency. Hence, in general, the voltage $V_{out}$ is higher than the voltage $V_{MCU}$. For this reason, in the control device 200A, the voltage $V_{out}$ is higher than the voltage $V_{op\text{-}amp}$ equal to the voltage $V_{MCU}$. Hence, the control device 200A is formed by at least a first region (for example, a region indicated by 290, although it is not necessarily limited) where the maximum voltage is $V_{out}$ and a second region (for example, a region indicated by 292, although it is not necessarily limited) where the maximum voltage is $V_{MCU}$. As described above, the maximum voltage $V_{MCU}$ in the second region is lower than the maximum voltage $V_{out}$ in the first region.

Note that unless a boosting device exists in each region, the maximum voltage equals the voltage applied to the entire region. That is, as described above, it can be said that the voltage $V_{MCU}$ applied to the second region is lower than the voltage $V_{out}$ applied to the first region.

The circuit 134 shown in FIGS. 1A and 1B electrically connects the power supply 110 and the load 132, and can include the first circuit 202 and the second circuit 204. The first circuit 202 and the second circuit 204 are electrically connected in parallel between the power supply 110 and the load 132. The first circuit 202 can include the switch Q1. The second circuit 204 can include the switch Q2 and the first shunt resistor 212. Hence, the first circuit 202 can have an electrical resistance value smaller than that of the second circuit 204. The circuit from the first circuit 202 to the load 132 forms at least a part of an aerosol generation circuit.

As indicated by dotted arrows in FIGS. 2A and 2B, the control unit 106 can control the switch Q1, the switch Q2, and the like, and can acquire values detected by the sensor 112A and the sensor 112C. The control unit 106 may be configured to cause the first circuit 202 to function by switching the switch Q1 from an OFF state to an ON state and cause the second circuit 204 to function by switching the switch Q2 from an OFF state to an ON state. The control unit 106 may be configured to cause the first circuit 202 and the second circuit 204 to alternately function by alternately switching the switches Q1 and Q2.

The first circuit 202 is mainly used to atomize the aerosol source. When the switch Q1 is switched to the ON state, and the first circuit 202 functions, power is supplied to the load 132, and the load 132 is heated. By heating the load 132, the aerosol source held by the holding portion 130 in the atomization unit 118A (in the aerosol inhalation device 100B shown in FIG. 1B, the aerosol source carried by the aerosol base material 116B) is atomized, and an aerosol is generated.

The second circuit 204 is used to acquire, for example, the value of a voltage according to a voltage applied to the load 132.

The operational amplifier 262 is used to form a voltage sensor that forms a part of the sensor 112. In the control device 200A, the operational amplifier 262 forms a part of an amplification circuit. Hence, the voltage $V_{analog}$ according to the voltage $V_{sample}$ (exactly, according to the difference between the voltage $V_{sample}$ and the voltage $V_{ref}$) is applied to the control unit 106. $V_{analog}$ may not be the difference itself between the voltage $V_{sample}$ and the voltage $V_{ref}$, and may be a voltage obtained by amplifying the difference between the voltage $V_{sample}$ and the voltage $V_{ref}$. Note that the power supply terminal (not shown) of the operational amplifier 262 may electrically be connected to ground. Additionally, in the control device 200A, the element electrically connected to the noninverting input terminal of the operational amplifier 262 and the element electrically connected to the inverting input terminal may be reversed. Hence, in some cases, the diode 268 is electrically connected to the inverting input terminal of the operational amplifier 262.

2-1-2 Second Shunt Resistor 252

The second shunt resistor 252 is used to stabilize the voltage $V_{sample}$ and the voltage $V_{analog}$ according to it when the load 132 is detached from the aerosol inhalation device 100 and reliably detect the detachment of the load 132, as will be described below in detail.

FIGS. 3A and 3B are circuit diagram showing some circuits of the control device 200A when the load 132 is attached or detached. In the following description, the switch Q1 is assumed to be in the OFF state, and the switch Q2 is assumed to be in the ON state.

When the load 132 is attached, the voltage $V_{sample}$ applied to the noninverting input terminal of the operational amplifier 262 is a voltage obtained by dividing the voltage $V_{out}$ by the first shunt resistor 212 and a combined resistor 340 (its electrical resistance value is represented by R') of the second shunt resistor 252, the resistor 254, and the load 132. That is, $$V_{sample} = \frac{R'}{R_{shunt1} + R'} \cdot V_{out} \tag{1}$$

Here.

$$\frac{1}{R'} = \frac{1}{R_{shunt2}} + \frac{1}{R_{connector} + R_{HTR}} \tag{2}$$

$$\frac{1}{R'} = \frac{R_{shunt2} + R_{connector} + R_{HTR}}{R_{shunt2} \cdot (R_{connector} + R_{HTR})}$$

-continued $$R' = \frac{R_{shunt2} \cdot (R_{connector} + R_{HTR})}{R_{shunt2} + R_{connector} + R_{HTR}}$$

On the other hand, when the load 132 is detached, the voltage $V_{sample}$ applied to the noninverting input terminal of the operational amplifier 262 is a voltage obtained by dividing the voltage $V_{out}$ by the first shunt resistor 212 and the second shunt resistor 252. That is, $$V_{sample} = \frac{R_{shunt2}}{R_{shunt1} + R_{shunt2}} \cdot V_{out} \quad (3)$$

As described above, the first shunt resistor 212 and the second shunt resistor 252 have electrical resistance values sufficiently larger than that of the resistor 254 or the load 132. Hence, since R' is obviously different from $R_{shunt2}$, based on equations (2), the voltage $V_{sample}$ changes between a state in which the load 132 is attached and a state in which the load 132 is detached, as can be seen from equations (1) and (3). Hence, the voltage $V_{analog}$ according to the voltage $V_{sample}$ also changes between the state in which the load 132 is attached and the state in which the load 132 is detached. This allows the control unit 106 to detect detachment of the load 132 based on the applied voltage.

Here, the circuits of the control device 200A in which the second shunt resistor 252 is assumed to be absent, as shown in FIG. 3C, will be examined. When the load 132 is detached, a path that starts from the power supply 110, passes through the first shunt resistor 212, and returns to the power supply 110 again does not form a closed circuit, and the value of the voltage $V_{analog}$ becomes unstable.

Hence, the accuracy in detecting the detachment of the load 132 can greatly be improved by providing the second shunt resistor 252.

2-1-3 Diode 268

The diode 268 is used to prevent an overvoltage from being applied to the noninverting input terminal of the operational amplifier 262, as will be described below in detail.

FIG. 3D is a circuit diagram showing some circuits of the control device 200A, for which the diode 268 is assumed to be absent.

First, a case in which the switch Q1 is in the ON state, and the switch Q2 is in the OFF state in the circuit shown in FIG. 3D will be examined. As is apparent from FIG. 2B, the voltage $V_{sample}$ equals the voltage $V_{out}$. Hence, $$V_{sample} = V_{out} \quad (4)$$

Additionally, as described above, since $$V_{op\text{-}amp} < V_{out} \quad (5)$$

we obtain, from inequalities (4) and (5)

$$V_{op\text{-}amp} < V_{sample} \quad (6)$$

This represents that the voltage $V_{sample}$ applied to the noninverting input terminal of the operational amplifier 262 becomes higher than the power supply voltage $V_{op\text{-}amp}$ of the operational amplifier 262. In this case, an overvoltage is applied to the noninverting input terminal of the operational amplifier 262, and the operational amplifier 262 may cause an operation error.

A case in which the switch Q1 is in the OFF state, and the switch Q2 is in the ON state in the circuit shown in FIG. 3D will be examined next. An electrical resistance value R of a combined resistor 342 of the first shunt resistor 212 and the combined resistor 340 (its electrical resistance value is represented by R') of the second shunt resistor 252, the resistor 254, and the load 132 is given by $$R = R_{shunt1} + R' \quad (7)$$

Since the electrical resistance value R' of the combined resistor 340 is represented by equations (2), the electrical resistance value R of the combined resistor 342 is given by $$R = R_{shunt1} + \frac{R_{shunt2} \cdot (R_{connector} + R_{HTR})}{R_{shunt2} + R_{connector} + R_{HTR}} \quad (8)$$

Letting I be the current flowing to the first shunt resistor 212, I is given by $$I = V_{out}/R \quad (9)$$

Since the voltage drop in the first shunt resistor 212 is $I \cdot R_{shunt1}$, the voltage $V_{sample}$ can be represented by $$\begin{aligned} V_{sample} &= V_{out} - I \cdot R_{shunt1} \\ &= V_{out} - \frac{V_{out}}{R} \cdot R_{shunt1} \\ &= V_{out} - V_{out} \cdot R_{shunt1} \cdot \left\{ R_{shunt1} + \frac{R_{shunt2} \cdot (R_{connector} + R_{HTR})}{R_{shunt2} + R_{connector} + R_{HTR}} \right\}^{-1} \\ &= V_{out} - V_{out} \cdot \left\{ 1 + \frac{R_{shunt2} \cdot (R_{connector} + R_{HTR})}{R_{shunt1} \cdot (R_{shunt2} + R_{connector} + R_{HTR})} \right\}^{-1} \end{aligned} \quad (10)$$

According to equation (10), if $R_{shunt1}$ and $R_{shunt2}$ are much larger than $R_{connector}$ and $R_{HTR}$, the voltage $V_{sample}$ applied to the noninverting input terminal of the operational amplifier 262 has a sufficiently small value. Hence, $V_{sample}$ does not become higher than the power supply voltage $V_{op\text{-}amp}$ of the operational amplifier 262. Otherwise, however, the voltage $V_{sample}$ applied to the noninverting input terminal of the operational amplifier 262 becomes higher than the power supply voltage $V_{op\text{-}amp}$ of the operational amplifier 262. That is, even if the switch Q1 is in the OFF state, and the switch Q2 is in the ON state, the voltage $V_{sample}$ applied to the noninverting input terminal of the operational amplifier 262 may be excessive.

Figure 3E:
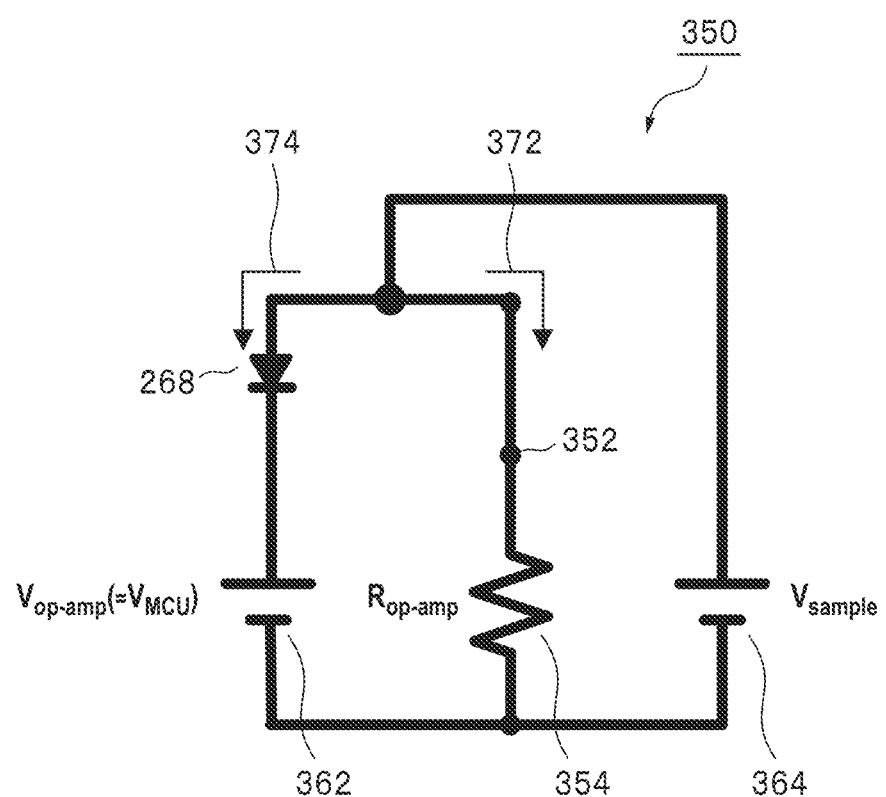

FIG. 3E shows an equivalent circuit 350 concerning the diode 268 in the control device 200A, which is configured to solve the problem of the excessive voltage.

Reference numeral 352 corresponds to the noninverting input terminal of the operational amplifier 262, and 354 corresponds to the substantial resistance (its electrical resistance value will be represented by $R_{op\text{-}amp}$ hereinafter) of the operational amplifier 262. Reference numerals 362 and 364 correspond to voltage sources that generate $V_{op\text{-}amp}$ and $V_{sample}$, respectively.

If the voltage $V_{op\text{-}amp}$ is almost higher than the voltage $V_{sample}$, no forward current flows to the diode 268. Hence, the current flows only in a direction indicated by 372. On the other hand, if the voltage $V_{sample}$ is almost higher than the voltage $V_{op\text{-}amp}$, a forward current flows to the diode 268. Here, if the electrical resistance value $R_{op\text{-}amp}$ of the resistor 354 is sufficiently larger than the electrical resistance value of the diode 268 in the forward direction, most of a current having an overvoltage flows to the diode 268.

If an excessively large current flows to the diode 268, the backflow preventing function of the diode 268 lowers, and a current generated by the voltage $V_{op\text{-}amp}$ may flow through the load 132. Hence, the current flowing to the diode 268 needs to be smaller than the maximum value depending on the diode 268. A condition to prevent the current flowing to the diode 268 from exceeding its maximum value will be examined below.

In the equivalent circuit 350, let $I_{F\_upper}$ be the maximum forward current permitted by the diode 268, and $R_F$ be the electrical resistance value of the diode 268 in the forward direction. If the following condition is satisfied, the current flowing to the diode 268 never exceeds its maximum value.

$$V_{sample} < I_{F\_upper} \cdot R_F + V_{op\text{-}amp} \quad (11)$$

Here, since the voltage $V_{sample}$ does not exceed the voltage $V_{out}$, as described above, after all, if the following condition is satisfied, the current flowing to the diode 268 never exceeds its maximum value, and the backflow preventing function of the diode 268 does not lower.

$$V_{out} < I_{F\_upper} \cdot R_F + V_{op\text{-}amp} \quad (12)$$

As described above, the smaller the value of $V_{out}$ is, the smaller the forward current of the diode 268 is. As a result, the diode 268 can be protected. However, in the ON state of the switch Q1, $V_{out}$ is applied to the load 132 for generating the aerosol. Hence, if $V_{out}$ is made too low, the load 132 may be unable to generate the aerosol.

Hence, $V_{out}$ needs to simultaneously satisfy the above-described condition of inequality (12) and a condition that the load 132 can generate the aerosol by the voltage. It was found as a result of earnest examinations of the present inventors that if the load 132 has an electrical resistance value of about 2.4Ω at room temperature, and $V_{out}$ is about 3.3 to 3.7 V, the above-described two conditions are simultaneously satisfied. It was also found that if the load 132 has an electrical resistance value of about 1.0Ω at room temperature, and $V_{out}$ is about 2.1 to 2.5 V, the above-described two conditions are simultaneously satisfied.

In the above-described embodiment, a circuit arrangement that makes the input voltage $V_{sample}$ of the operational amplifier 262 equal to or lower than the power supply voltage $V_{op\text{-}amp}$ of the operational amplifier 262 has been described. The same problem can occur when a comparator is used in place of the operational amplifier 262. Even in this case, the input voltage of the comparator can be made equal to or lower than the power supply voltage of the comparator by using the diode 268 whose anode is connected to the input terminal of the comparator.

2-2 Second Control Device
2-2-1 Circuit Arrangement

Figure 2D:
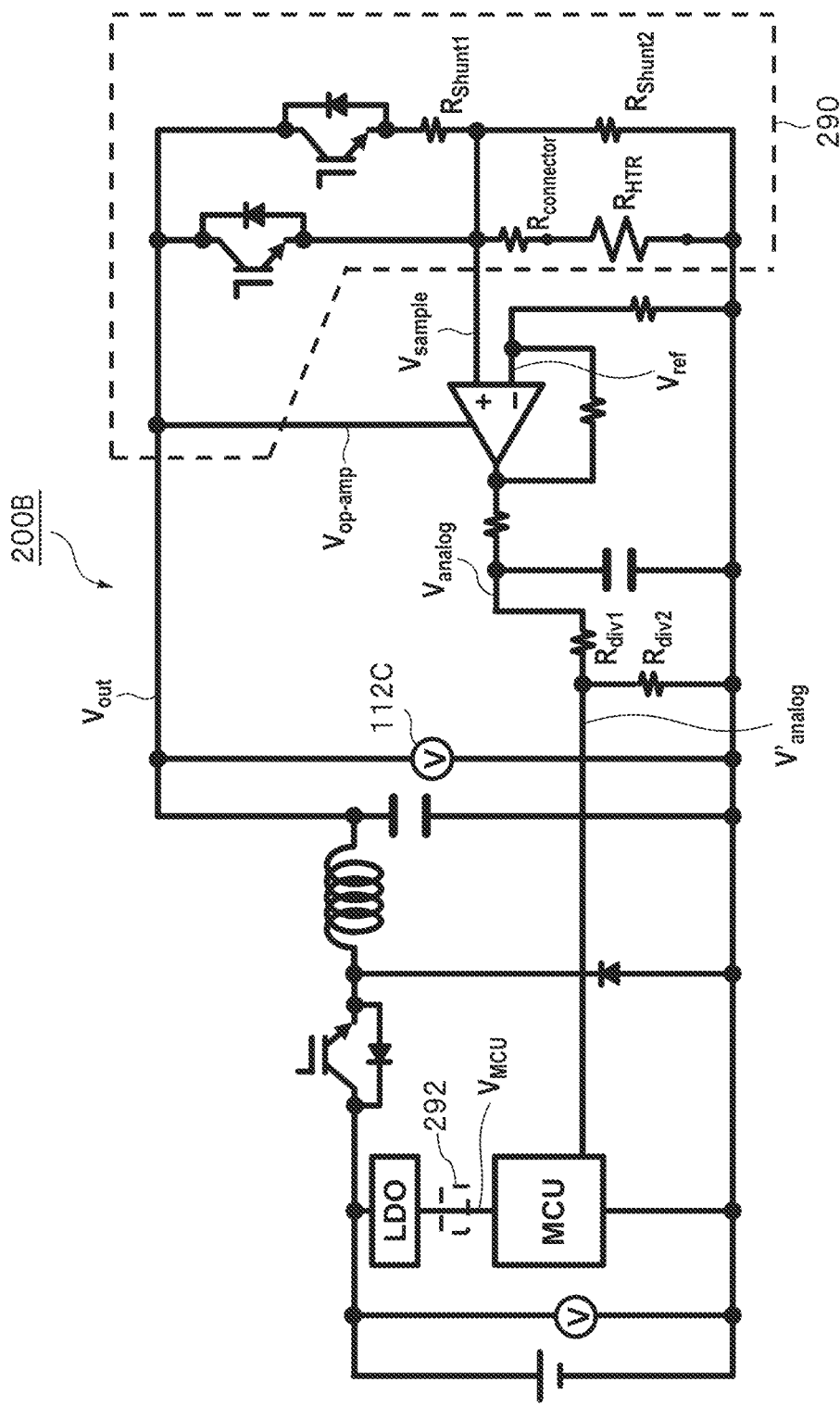

FIGS. 2C and 2D are circuit diagrams showing the schematic circuit arrangement of a control device 200B for the aerosol inhalation device 100 according to another embodiment of the present invention. Reference numerals used to mention the elements of the control device 200B are added in FIG. 2C, and reference symbols and the like concerning voltages and electrical resistance values used in the description are added in FIG. 2D. The control device 200A and the control device 200B have some common components, and the same reference numerals denote the same components in FIGS. 2A and 2B and FIGS. 2C and 2D. Differences of the control device 200B from the control device 200A will be described below.

In the control device 200B, the diode 268 does not exist, and the voltage $V_{out}$ is applied to the power supply terminal of the operational amplifier 262. Hence, in the control device 200B, the voltage $V_{op\text{-}amp}$ applied to the power supply terminal of the operational amplifier 262 equals $V_{out}$.

Also, the control device 200B includes a voltage dividing circuit 286 formed by a first resistor 282 and a second resistor 284 (their electrical resistance values will be represented by $R_{div1}$ and $R_{div2}$, respectively, hereinafter). The voltage dividing circuit 286 divides the voltage $V_{analog}$ and outputs a voltage $V'_{analog}$.

Further, in the control device 200B, the voltage $V_{analog}$ is input to the control unit 106.

2-2-2 Voltage Dividing Circuit 286

In the control device 200B, if the voltage dividing circuit 286 does not exist, the voltage $V_{analog}$ is applied to the control unit 106. Since the power supply voltage of the operational amplifier 262 in the control device 200B is $V_{out}$, the voltage $V_{analog}$ according to the output voltage of the operational amplifier 262 may also reach $V_{out}$. On the other hand, since the power supply voltage of the control unit 106 is $V_{MCU}$, and in general, $V_{MCU} < V_{out}$, as described above, the voltage $V_{analog}$ higher than $V_{MCU}$ that is the power supply voltage is applied to the control unit 106, and an overvoltage may occur.

The voltage dividing circuit 286 is configured to prevent the above-described problem. In the control device 200B, the relationship between the voltage $V_{analog}$ and the voltage $V'_{analog}$ applied to the control unit 106 is represented by $$V'_{analog} = \frac{R_{div2}}{R_{div1} + R_{div2}} \cdot V_{analog} \quad (13)$$

To avoid input of the overvoltage to the control unit 106, the voltage $V'_{analog}$ input to the control unit 106 needs to be equal to or lower than the power supply voltage $V_{MCU}$. That is, $$V_{MCU} \geq V'_{analog} \geq \frac{R_{div2}}{R_{div1} + R_{div2}} \cdot V_{analog} \quad (14)$$

Let $A_d$ be the amplification factor of the amplification circuit formed by the operational amplifier 262 in the control device 200B. Then, we obtain $$V_{analog} = A_d \cdot (V_{sample} - V_{ref}) \quad (15)$$

Since the voltage $V_{sample}$ does not exceed the voltage $V_{out}$, $$V_{analog} \leq A_d \cdot (V_{out} - V_{ref}) \quad (16)$$

Based on inequalities (14) and (16), if the voltage $V_{MCU}$ and the voltage $V_{out}$ satisfy the following relationship, the above-described problem of the overvoltage does not occur.

$$V_{MCU} \geq \frac{R_{div2}}{R_{div1} + R_{div2}} \cdot V_{analog} \quad (17)$$

$$V_{MCU} \geq \frac{R_{div2}}{R_{div1} + R_{div2}} \cdot A_d \cdot (V_{out} - V_{ref})$$

$$\frac{R_{div1} + R_{div2}}{R_{div2}} \cdot \frac{1}{A_d} \cdot V_{MCU} \geq V_{out} - V_{ref} \quad (18)$$

$$V_{out} - V_{ref} \leq \frac{R_{div1} + R_{div2}}{R_{div2}} \cdot \frac{1}{A_d} \cdot V_{MCU}$$

$$V_{out} \leq \frac{R_{div1} + R_{div2}}{R_{div2}} \cdot \frac{1}{A_d} \cdot V_{MCU} + V_{ref}$$

Hence, application of the overvoltage to the control unit 106 can be prevented by performing one or both of adjusting the converter 208 to output $V_{out}$ satisfying inequalities (18)

and setting the electrical resistance values $R_{div1}$ and $R_{div2}$ of the first resistor 282 and the second resistor 284 of the voltage dividing circuit 286 to satisfy inequalities (18). From another viewpoint, according to inequalities (18), the upper limit value of the output voltage $V_{out}$ of the converter 208 in a case in which the electrical resistance values $R_{div1}$ and $R_{div2}$ of the first resistor 282 and the second resistor 284 of the voltage dividing circuit 286 are fixed is determined.

As described above, the smaller the value of $V_{out}$ is, the lower $V_{analog}$ is. As a result, the control unit 106 can be protected. However, in the ON state of the switch Q1, $V_{out}$ is applied to the load 132 for generating the aerosol. Hence, if $V_{out}$ is made too low, the load 132 may be unable to generate the aerosol. Hence, $V_{out}$ needs to simultaneously satisfy the above-described condition of inequalities (18) and a condition that the load 132 can generate the aerosol by the voltage. It was found as a result of earnest examinations of the present inventors that if the load 132 has an electrical resistance value of about 2.4Ω at room temperature, and $V_{out}$ is about 3.3 to 3.7 V, the above-described two conditions are simultaneously satisfied. It was also found that if the load 132 has an electrical resistance value of about 1.0Ω at room temperature, and $V_{out}$ is about 2.1 to 2.5 V, the above-described two conditions are simultaneously satisfied.

Figure 4A:
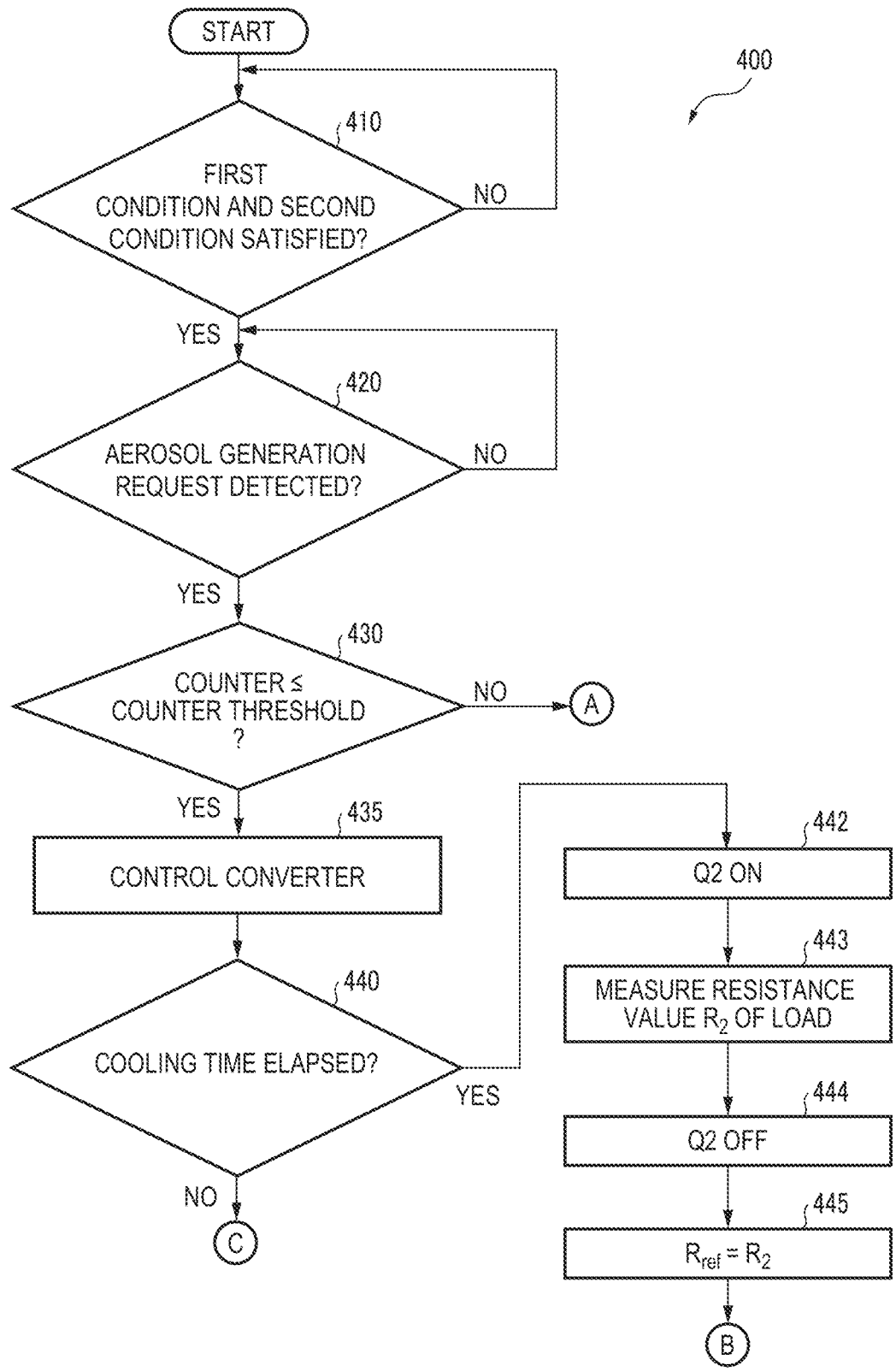
Figures 2, 4A:
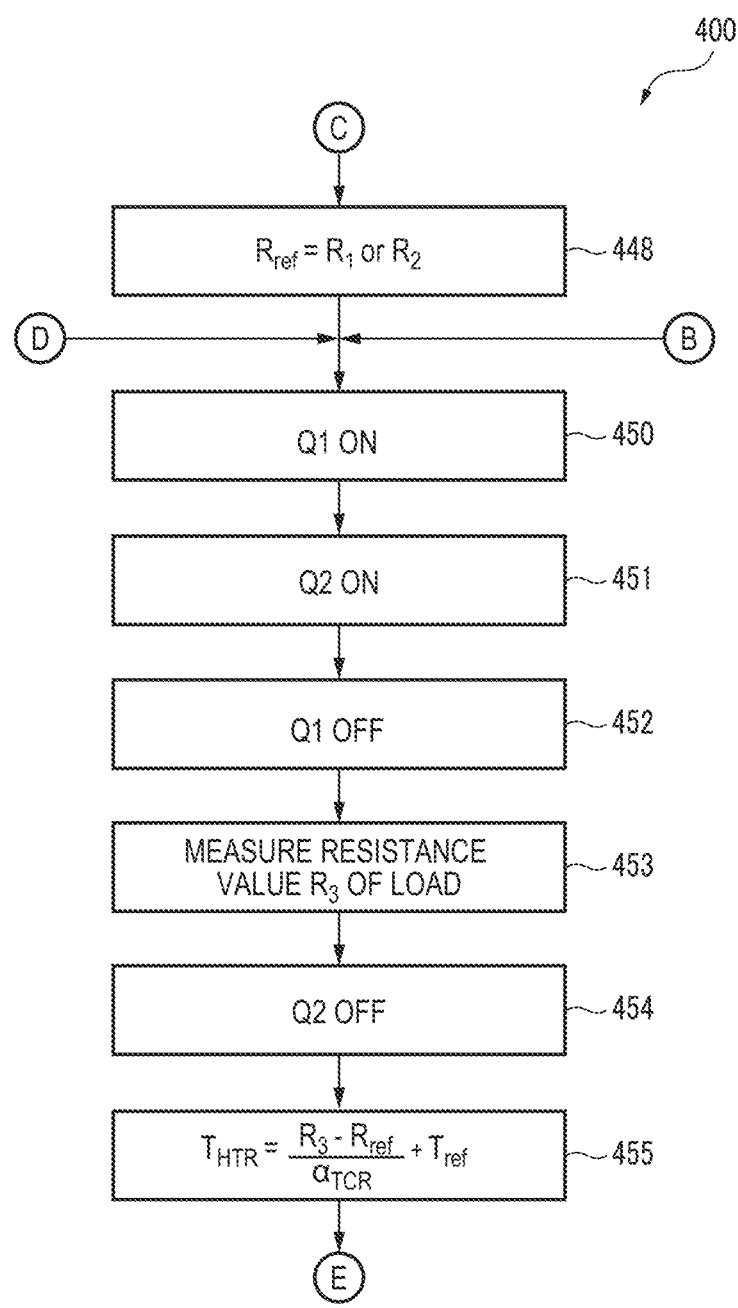
Figure 4B:
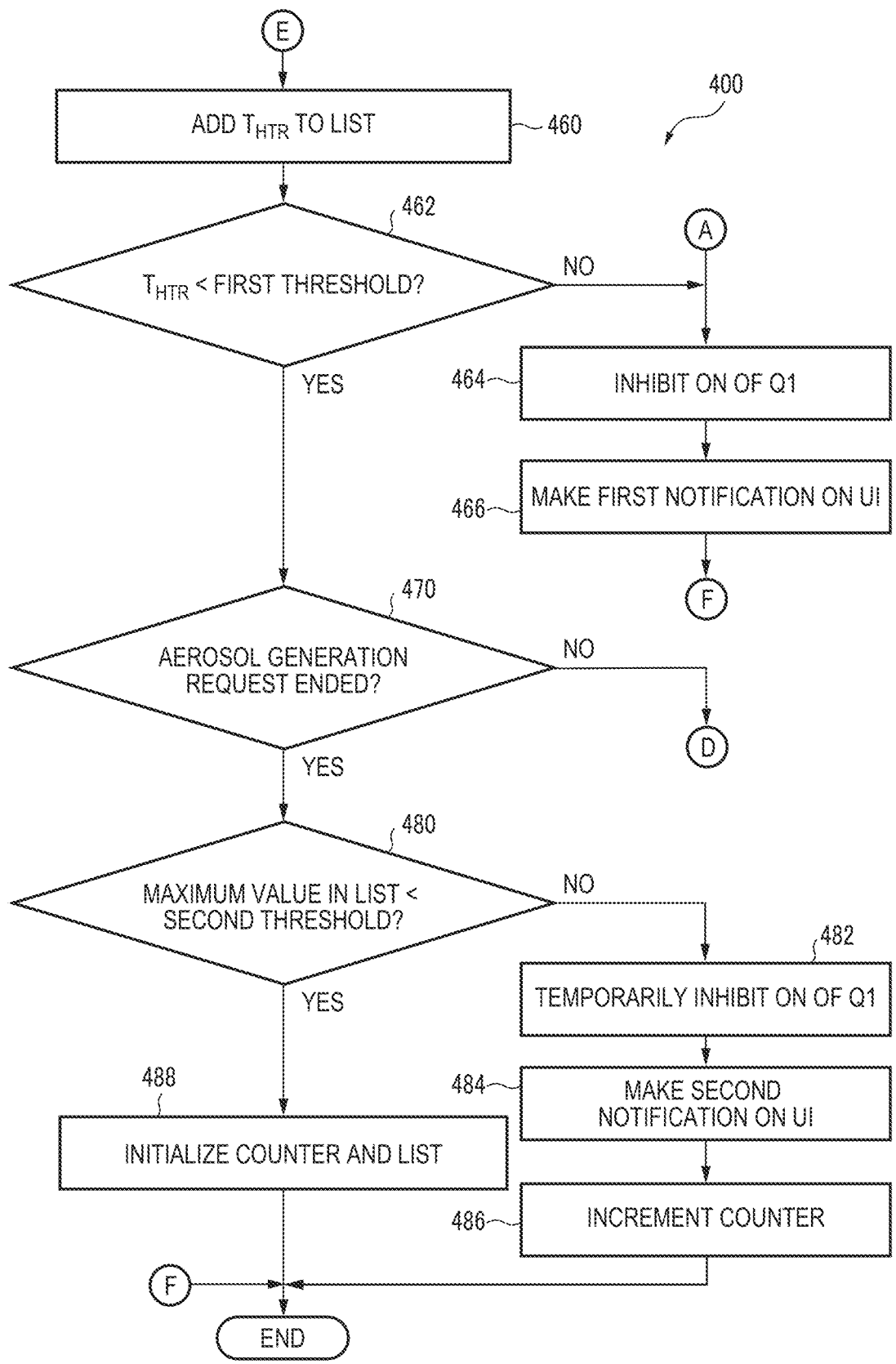

3 OPERATION OF CONTROL DEVICE FOR AEROSOL INHALATION DEVICE 3-1 Main Processing FIGS. 4A, 4A-2 and 4B are flowcharts of exemplary main processing 400 for measuring the temperature of the load 132 and detecting the remaining amount of the aerosol source. Note that the main processing 400 is executed by the control device 200A or the control unit 106 included in the control device 200A, and repeated during the operation of the aerosol inhalation device 100.

Step 410 represents a step of determining whether a first condition and a second condition are satisfied. Upon determining that the first condition and the second condition are satisfied, the process advances to step 420. Otherwise, step 410 is repeated. The first condition and the second condition will be described later.

In subsequent step 450 to be described later, a signal used to set the switch Q1 in the ON state to atomize the aerosol source is transmitted. If at least one of the first condition and the second condition is not satisfied in step 410, the process does not advance to step 450. Hence, setting the switch Q1 in the ON state is inhibited.

Step 420 represents a step of determining whether an aerosol generation request is detected. Upon determining that the aerosol generation request is detected, the process advances to step 430. Otherwise, step 420 is repeated.

Upon detecting the start of inhalation by the user based on information obtained from, for example, a pressure sensor, a flow velocity sensor, a flow rate sensor, or the like, the control unit 106 can determine that the aerosol generation request is detected. More specifically, for example, if the output value of the pressure sensor, that is, the pressure is lower than a predetermined threshold, the control unit 106 can determine that the start of inhalation by the user is detected. Alternatively, for example, if the output value of the flow velocity sensor or the flow rate sensor, that is, the flow velocity or the flow rate is higher than a predetermined threshold, the control unit 106 can determine that the start of inhalation by the user is detected. Since this determination method enables aerosol generation according to user's feeling, the flow velocity sensor or the flow rate sensor is particularly preferable. Alternatively, if the output values of these sensors start continuously changing, the control unit 106 may determine that the start of inhalation by the user is detected. Otherwise, based on pressing of a button used to start aerosol generation, or the like, the control unit 106 may determine that the start of inhalation by the user is detected. Alternatively, based on both the information obtained from the pressure sensor, the flow velocity sensor, or the flow rate sensor and pressing of the button, the control unit 106 may determine that the start of inhalation by the user is detected.

Step 430 represents a step of determining whether a counter is equal to or less than a predetermined counter threshold. If the counter is equal to or less than the predetermined counter threshold, the process advances to step 440. Otherwise, the process advances to step 464 shown in FIG. 4B to be described later.

The predetermined counter threshold can be one or more predetermined values. The significance of step 430 will be described later.

Step 435 represents a step of controlling the converter 208 to generate the voltage $V_{out}$ set in step 534 to be described later. This step can be a step of performing nothing if the converter 208 is already outputting the voltage $V_{out}$. Also, this step can be executed at any timing before power is supplied to the load 132.

Step 440 represents a step of determining whether a predetermined cooling time has elapsed from the stop of power feed to the load 132. Upon determining that the predetermined cooling time has elapsed from the stop of power feed to the load 132, the process advances to step 442. Otherwise, the process advances to step 448.

Step 442 represents a step of transmitting a signal used to set the switch Q2 in the ON state to acquire the electrical resistance value of the load 132.

Step 443 represents a step of acquiring the electrical resistance value of the load 132 as $R_2$ based on the voltage $V_{analog}$ or the voltage $V'_{analog}$ applied to the control unit 106 and at least temporarily storing the electrical resistance value in the memory 114. As will be described later, the electrical resistance value $R_2$ is used to calibrate the correlation between the electrical resistance value and the temperature of the load 132.

The method of obtaining the electrical resistance value of the load 132 based on the voltage $V_{analog}$ or the voltage $V'_{analog}$ is arbitrary. For example, the electrical resistance value of the load 132 is the function of the value of the voltage $V_{analog}$ or the voltage $V'_{analog}$. Hence, the function is obtained in advance experimentally or by calculations, and in step 443, the electrical resistance value of the load 132 can be acquired in accordance with the function.

Note that since the voltage $V_{analog}$ or the voltage $V_{analog}$ is the voltage according to the output of the operational amplifier 262, the processing of acquiring the electrical resistance value of the load 132 based on the voltage $V_{analog}$ or the voltage $V'_{analog}$ is processing based on the output of the operational amplifier 262.

In addition, the processing of acquiring the electrical resistance value of the load 132 based on the voltage $V_{analog}$ or the voltage $V'_{analog}$ is obviously processing based on the voltage applied to the control unit 106.

Step 444 represents a step of transmitting a signal used to set the switch Q2 in the OFF state.

Step 445 represents a step of substituting the electrical resistance value $R_2$ acquired in immediately preceding step 443 into a variable representing a reference resistance value $R_{ref}$ to calibrate the correlation between the electrical resistance value and the temperature of the load 132 to acquire the temperature of the load 132 in step 455 to be described later.

Step 448 represents a step of substituting one of the electrical resistance values $R_2$ acquired in step 443 before the immediately preceding step or the value of an electrical resistance value $R_1$ of the load 132 acquired at the time of exchange of the cartridge 104A to be described later into the variable representing the reference resistance value $R_{ref}$.

Note that if the value of the variable representing the reference resistance value $R_{ref}$ during the operation of the aerosol inhalation device 100 is held, step 448 may be a step of substituting the value of the electrical resistance value $R_1$ into the variable in a case in which the value of the variable representing the reference resistance value $R_{ref}$ is not set, and otherwise, performing nothing.

Note that the substitution in step 445 and step 448 is processing for improving the accuracy of a temperature $T_{HTR}$ of the load 132 calculated by an equation used in step 455 to be described later, which represents the correlation between the electrical resistance value and the temperature of the load 132, and is an example of processing of calibrating the correlation.

Step 450 represents a step of transmitting a signal used to set the switch Q1 in the ON state to atomize the aerosol source.

Step 451 represents a step of transmitting a signal used to set the switch Q2 in the ON state to acquire the electrical resistance value of the load 132, and step 452 represents a step of transmitting a signal used to set the switch Q1 in the OFF state to accurately acquire the electrical resistance value of the load 132. It does not matter which of steps 451 and 452 is executed first, and the steps may be executed simultaneously. If a delay from the transmission of the signal to the switch to the actual change of the state is taken into consideration, step 451 is preferably performed before step 452.

Step 453 represents a step of acquiring the electrical resistance value of the load 132 as $R_3$ based on the voltage $V_{analog}$ or the voltage $V'_{analog}$ applied to the control unit 106.

Step 454 represents a step of transmitting a signal used to set the switch Q2 in the OFF state.

Step 455 represents a step of acquiring the temperature $T_{HTR}$ of the load 132. The value of the temperature $T_{HTR}$ of the load 132 can be obtain by $$T_{HTR} = \frac{R3 - R_{ref}}{\alpha_{TCR}} + T_{ref} \quad (19)$$

where Tref is a predetermined reference temperature, and is preferably a temperature equal to the temperature of the load 132 when its electrical resistance value is $R_{ref}$ or a temperature close to the temperature. For example, when $T_{ref}$ is set to an ambient temperature (for example, room temperature or 25° C.) at which the aerosol inhalation device 100 is assumed to be used, the temperature of the load 132 at the time of execution of step 443 or step 530 to be described later will be a temperature near $T_{ref}$. $\alpha_{TCR}$ is a known constant depending on the material of the load 132.

Note that as described above, the processing of acquiring $R_{ref}$ and $R_3$ in equation (19) is processing based on the voltage according to the output of the operational amplifier 262. Hence, the processing of acquiring the temperature $T_{HTR}$ of the load 132 in accordance with equation (19) is processing based on the voltage according to the output of the operational amplifier 262. Similarly, the processing of acquiring the temperature $T_{HTR}$ of the load 132 in accordance with equation (19) is also processing based on the voltage applied to the control unit 106.

Step 460 represents a step of adding the temperature $T_{HTR}$ of the load 132 acquired in preceding step 455 to a list that is a data structure and making the temperature referable later. Note that the list is merely an example, and in step 460, an arbitrary data structure capable of holding a plurality of data such as an array can be used. Note that unless it is judged in step 470 to be described later that the process should advance to step 480, the process of step 460 is executed a plurality of times. If step 460 is executed a plurality of times, the temperature $T_{HTR}$ of the load 132 in the data structure is not overwritten but added as many as the number of times of execution of the process of step 460.

Step 462 represents a step of determining whether the temperature $T_{HTR}$ of the load 132 acquired in immediately preceding step 455 is lower than a predetermined first threshold. If the temperature $T_{HTR}$ of the load 132 is lower than the first threshold, the process advances to step 470. Otherwise, the process advances to step 464.

The first threshold is preferably a temperature at which exhaustion of the aerosol source is strongly suspected when the temperature of the load 132 exceeds it, and is, for example, 300° C.

Step 464 represents a step of inhibiting the switch Q1 from changing to the ON state.

This step can be a step of setting a flag concerning the first condition in the memory 114, and this flag can be canceled when the cartridge 104A is exchanged. That is, in this example, the first condition is that the cartridge 104A is exchanged. Until the flag is canceled, that is, until the cartridge 104A is exchanged, the first condition is not satisfied, and the determination in step 410 is false. In other words, unless the flag is canceled, the determination in step 410 never becomes true.

Note that steps 462 and 464 are processes based on the temperature $T_{HTR}$ of the load 132, and as described above, the processing of acquiring the temperature $T_{HTR}$ of the load 132 in accordance with equation (19) is processing based on the voltage according to the output of the operational amplifier 262. Hence, the processing concerning steps 462 and 464 can be processing based on the voltage according to the output of the operational amplifier 262. Similarly, the processing concerning steps 462 and 464 can also be processing based on the voltage applied to the control unit 106.

Step 466 represents a step of making a predetermined notification on a UI (user interface) on the notification unit 108.

This notification can be a notification representing that the cartridge 104A should be exchanged.

Step 470 represents a step of determining whether the aerosol generation request has ended. Upon determining that the aerosol generation request has ended, the process advances to step 480. Otherwise, the process returns to step 450.

Upon detecting the end of inhalation by the user based on information obtained from, for example, a pressure sensor, a flow velocity sensor, a flow rate sensor, or the like, the control unit 106 can determine that the aerosol generation request has ended. Here, for example, if the output value of the pressure sensor, that is, the pressure exceeds a predetermined threshold, the control unit 106 can determine that the end of inhalation by the user is detected, in other words, aerosol generation is not requested. Alternatively, for example, if the output value of the flow velocity sensor or the flow rate sensor, that is, the flow velocity or the flow rate is lower than a predetermined threshold, the control unit 106 can determine that the end of inhalation by the user is detected, in other words, aerosol generation is not requested. Note that the threshold may be larger than the threshold in step 420, equal to the threshold, or smaller than the threshold. Otherwise, based on release of a button used to start aerosol generation, or the like, the control unit 106 may determine that the end of inhalation by the user is detected, in other words, aerosol generation is not requested. Alternatively, if a predetermined condition that, for example, a predetermined time has elapsed from the pressing of the button used to start aerosol generation is satisfied, the control unit 106 may determine that the end of inhalation by the user is detected, in other words, aerosol generation is not requested.

Step 480 represents a step of determining whether the maximum value in the list that holds one or more temperatures $T_{HTR}$ of the load 132 is smaller than a predetermined second threshold. If the maximum value is smaller than the second threshold, the process advances to step 488. Otherwise, the process advances to step 482.

The second threshold is preferably a temperature at which exhaustion of the aerosol source is suspected when the temperature of the load 132 exceeds it, but at which there is also a possibility of temporary shortage of the aerosol source in the holding portion 130 due to, for example, a delay of aerosol source supply from the storage unit 116A. Hence, the second threshold can be smaller than the first threshold and is, for example, 250° C.

Step 482 represents a step of temporarily inhibiting the switch Q1 from changing to the ON state.

This step can be a step of setting a flag concerning the second condition in the memory 114, and this flag can be canceled when a predetermined time has elapsed from setting of the flag. That is, in this example, the second condition is that a predetermined time elapses from setting of the flag. Until the flag is canceled, that is, until a predetermined time has elapsed from setting of the flag, the second condition is not satisfied, and the determination in step 410 is temporarily false. In other words, unless the flag is canceled, the determination in step 410 never becomes true. Note that the predetermined time can be 10 sec or more, for example, 11 sec.

Note that steps 480 and 482 are processes based on the temperature $T_{HTR}$ of the load 132, and as described above, the processing of acquiring the temperature $T_{HTR}$ of the load 132 in accordance with equation (19) is processing based on the voltage according to the output of the operational amplifier 262. Hence, the processing concerning steps 480 and 482 can be processing based on the voltage according to the output of the operational amplifier 262. Similarly, the processing concerning steps 480 and 482 can also be processing based on the voltage applied to the control unit 106.

Step 484 represents a step of making a predetermined notification on the UI on the notification unit 108.

This notification can be a notification that promotes the user to wait for inhalation of the aerosol for a while.

Step 486 represents a step of, for example, incrementing the counter by one.

Step 488 represents a step of initializing the counter and the list. By this step, the counter can be 0, and the list can be made empty.

In this embodiment, in step 480 after the aerosol generation request has ended, the temperature $T_{HTR}$ of the load 132 is compared with the second threshold. In place of this embodiment, the temperature $T_{HTR}$ of the load 132 may be compared with the second threshold before the aerosol generation request ends. In this case, if it is judged that the temperature $T_{HTR}$ of the load 132 is equal to or higher than the second threshold, comparison between the second threshold and the temperature $T_{HTR}$ of the load 132 need not be performed any more until the aerosol generation request ends.

3-2 Auxiliary Processing

FIG. 5 is a flowchart of exemplary processing 500 for supporting the main processing 400. The auxiliary processing 500 can be executed simultaneously with or in parallel to the main processing 400.

Step 510 represents a step of determining whether exchange of the cartridge 104A is detected. Since the cartridge 104A includes the load 132, as described in 2-1-2, the control unit 106 detects attachment/detachment of the load 132 based on the voltage $V_{analog}$ (or the voltage $V'_{analog}$), thereby detecting exchange of the cartridge 104A. If exchange of the cartridge 104A is detected, the process advances to step 520. Otherwise, step 510 is repeated.

Step 520 represents a step of transmitting a signal used to set the switch Q2 in the ON state to acquire the electrical resistance value of the load 132.

Step 530 represents a step of acquiring the electrical resistance value of the load 132 as $R_1$ based on the voltage $V_{analog}$ or the voltage $V'_{analog}$ applied to the control unit 106 and at least temporarily storing it in the memory 114.

Step 532 represents a step of identifying the type of the exchanged cartridge 104A. Identifying the type of the cartridge 104A includes specifying, based on the electrical resistance value $R_1$ acquired in step 530, the type (including a material, for example, Nichrome or SUS) of the load 132 included in the cartridge.

Step 534 represents a step of setting the output voltage $V_{out}$ optimum for the load 132 based on the specified type of the load 132.

In the embodiment as described in 2-1 in which the input voltage $V_{sample}$ of the operational amplifier 262 can be higher than the power supply voltage $V_{op-amp}$ of the operational amplifier 262, the optimum output voltage $V_{out}$ is preferably a voltage that prevents an operation error caused by the overvoltage of the diode 268 and allows the load 132 to generate the aerosol. More specifically, the optimum output voltage $V_{out}$ is preferably a voltage that prevents the forward voltage flowing to the diode 268 from exceeding an allowable value and allows the load 132 to generate the aerosol.

In the embodiment as described in 2-2 in which the voltage $V_{analog}$ input to the control unit 106 can be higher than the power supply voltage $V_{MCU}$ of the control unit 106, the optimum output voltage $V_{out}$ is preferably a voltage that prevents an operation error caused by the overvoltage of the control unit 106 and allows the load 132 to generate the aerosol. More specifically, it is preferably a voltage that makes the voltage $V_{analog}$ or the voltage $V'_{analog}$ input to the control unit 106 equal to or lower than the power supply voltage $V_{MCU}$ of the control unit 106 and allows the load 132 to generate the aerosol.

It was found as a result of earnest examinations of the present inventors that if the load 132 has an electrical resistance value of about 2.4Ω at room temperature, and $V_{out}$ is about 3.3 to 3.7 V, conditions that the above-described optimum output voltage $V_{out}$ should satisfy are satisfied. It was also found that if the load 132 has an electrical resistance value of about 1.0Ω at room temperature, and $V_{out}$ is about 2.1 to 2.5 V, the above-described two conditions are simultaneously satisfied.

In this way, the plurality of optimum output voltages $V_{out}$ or the range of the optimum output voltages $V_{out}$ is determined in accordance with the type of the load 132. The converter 208 can be configured to output the plurality of voltages or the voltages in the range in accordance with the type of the load 132.

Note that steps 532 and 534 are processed based on $R_1$, and processing of acquiring $R_1$ is processing based on the voltage according to the output of the operational amplifier 262. Hence, the processing concerning steps 532 and 534 is processing based on the voltage according to the output of the operational amplifier 262. Similarly, the processing concerning steps 532 and 534 is also processing based on the voltage applied to the control unit 106.

Step 540 represents a step of transmitting a signal used to set the switch Q2 in the OFF state.

Step 550 represents a step of initializing the above-described counter and list used in the main processing 400.

Steps 462, 480, and 510 described above can be implemented by converting an analog signal that is the voltage according to the output of the operational amplifier 262 to a digital value by an A/D converter provided in the control unit 106 and comparing it with a predetermined threshold. In place of this method, steps 462, 480, and 510 described above can also be implemented by using a comparator in place of the operational amplifier 262 and setting the reference voltage of the comparator to a value corresponding to a predetermined threshold. It would be obvious for those skilled in the art that even in a case in which a comparator is used, the comparator or the control unit can be protected from an overvoltage by the above-described diode 268 or the voltage dividing circuit 286.

4 CONCLUSION

While the embodiments of the present invention have been described above, it is to be understood that the embodiments are merely examples, and do not limit the scope of the present invention. It should be understood that modifications, additions, improvements, and the like of the embodiments can appropriately be made without departing from the spirit and scope of the present invention. The scope of the present invention should not be limited by any of the above-described embodiments, and should be limited only by the appended claims and their equivalents.

REFERENCE SIGNS LIST 100A, 100B . . . aerosol inhalation device
102 . . . main body
104A . . . cartridge
104B . . . aerosol generating article
106 . . . control unit (for example, MCU)
108 . . . notification unit
110 . . . power supply
112, 112A, 112C . . . sensor
114 . . . memory
116A . . . storage unit
116B . . . aerosol base material
118A, 118B . . . atomization unit
120 . . . air intake channel
121 . . . aerosol channel
122 . . . mouthpiece portion
130 . . . holding portion
132 . . . load
134 . . . circuit
200A, 200B . . . control device for aerosol inhalation device
202 . . . first circuit
204 . . . second circuit
206, 210, 214 . . . FET
208 . . . converter (for example, switching regulator)
212 . . . first shunt resistor
216 . . . diode
218 . . . inductor
220 . . . capacitor
242 . . . regulator (for example, LDO)
252 . . . second shunt resistor
254 . . . resistor
256, 258 . . . connection terminal
262 . . . operational amplifier
264, 266 . . . resistor
268 . . . diode
272 . . . resistor
274 . . . capacitor
282, 284 . . . resistor that forms voltage dividing circuit
286 . . . voltage dividing circuit
340, 342 . . . combined resistor
350 . . . equivalent circuit
352 . . . noninverting input terminal of operational amplifier
354 . . . resistor provided in operational amplifier
362, 364 . . . voltage source
372, 374 . . . flow of current

What is claimed is:

1. An aerosol inhalation device, the aerosol inhalation device comprising:
an operational amplifier including an output terminal configured to generate a voltage according to a power applied to a load configured to heat an aerosol source and having a correlation between a temperature and an electrical resistance value;
a controller including an input terminal and configured to perform processing based on a voltage applied to the input terminal;
an RC circuit connected to the output terminal of the operational amplifier and configured to generate a voltage supplied to the input terminal of the controller;
a first switch electrically connected between the power supply and the load;
a second switch electrically connected in parallel between the power supply and the load; and
a first resistor electrically connected in series with the first switch, wherein
a power supply voltage of the operational amplifier is higher than a power supply voltage of the controller, and equals a voltage applied to an aerosol generation circuit including the load, and
one of an inverting input terminal and a noninverting input terminal of the operational amplifier is electrically connected to the aerosol generation circuit.

2. The device according to claim 1, wherein the RC circuit is configured such that the voltage applied to the input terminal of the controller is not more than a power supply voltage of the controller.

3. The device according to claim 1, wherein an amplification factor of the operational amplifier is set such that the voltage applied to the input terminal of the controller is not more than the power supply voltage of the controller.

4. The device according to claim 1, further comprising:
a converter configured to apply a predetermined voltage to the aerosol generation circuit including the load.

5. The device according to claim 4, wherein
an output terminal of the converter is electrically connected to the aerosol generation circuit and a power supply terminal of the operational amplifier, and
one of an inverting input terminal and a noninverting input terminal of the operational amplifier is electrically connected to the aerosol generation circuit.

6. The device according to claim 4, wherein
the converter is configured to output a voltage that makes the voltage applied to the input terminal of the controller not more than a power supply voltage of the controller and allows the load to generate an aerosol.

7. The device according to claim 6, wherein
the voltage dividing circuit is configured such that the voltage applied to the input terminal of the controller is not more than the power supply voltage of the controller.

8. The device according to claim 4, wherein
the converter comprises a switching regulator.

9. The device according to claim 4, wherein
the converter is configured to output a plurality of voltages or voltages in a range, the voltages making the voltage applied to the input terminal of the controller not more than a power supply voltage of the controller and allowing the load to generate an aerosol.

10. The device according to claim 9, wherein
the controller is configured to adjust an output voltage of the converter in accordance with a type of the load.

11. The device according to claim 1, wherein
an electrical resistance value of a path between the power supply and the load passing through the second switch is larger than an electrical resistance value of a path between the power supply and the load passing through the first switch, and
the controller is further configured to acquire the voltage applied to the input terminal during a time when the second switch is in an ON state.

12. The device according to claim 11, wherein
the controller is configured to set the first switch in the ON state to generate an aerosol.

13. The device according to claim 11, further comprising:
a second resistor electrically connected in series with the second switch such that the second switch and the second resistor are electrically connected in parallel with the first switch.

14. The device according to claim 13, wherein
an electrical resistance value of the first resistor is equal to an electrical resistance value of the second resistor.

* * * * *